US010206799B2

(12) United States Patent
Zimmerman et al.

(10) Patent No.: US 10,206,799 B2
(45) Date of Patent: Feb. 19, 2019

(54) DEVICE AND METHOD FOR INCREASING FLOW THROUGH THE LEFT ATRIAL APPENDAGE

(71) Applicant: Edwards Lifesciences Corporation, Irvine, CA (US)

(72) Inventors: Neil S. Zimmerman, Menlo Park, CA (US); Robert C. Taft, Irvine, CA (US); Eric R. Reuland, Laguna Niguel, CA (US); David L. Hauser, Newport Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/815,071

(22) Filed: Nov. 16, 2017

(65) Prior Publication Data

US 2018/0078394 A1  Mar. 22, 2018

Related U.S. Application Data

(60) Division of application No. 14/808,946, filed on Jul. 24, 2015, now Pat. No. 9,849,011, which is a
(Continued)

(51) Int. Cl.
*A61F 2/00* (2006.01)
*A61F 2/91* (2013.01)
(Continued)

(52) U.S. Cl.
CPC ............... *A61F 2/91* (2013.01); *A61F 2/07* (2013.01); *A61F 2/844* (2013.01); *A61F 2/848* (2013.01);
(Continued)

(58) Field of Classification Search
CPC ...... A61F 2/01; A61F 2/07; A61F 2/24; A61F 2/2493; A61F 2/844; A61F 2/848;
(Continued)

(56) References Cited

U.S. PATENT DOCUMENTS 6,730,108 B2   5/2004  Van Tassel et al.
7,806,846 B2  10/2010  Chanduszko et al.
(Continued)

FOREIGN PATENT DOCUMENTS

CN  1342056 A  3/2002
CN  1399531 A  2/2003
(Continued)

OTHER PUBLICATIONS

International Search Report for PCT/US2014/031505 dated Aug. 5, 2014.
(Continued)

*Primary Examiner* — Benjamin Klein
(74) *Attorney, Agent, or Firm* — Klarquist Sparkman LLP; Carsten C. Grellmann

(57) ABSTRACT

Methods and devices for increasing flow in the left atrial appendage (LAA) include a conduit directing blood flow from a pulmonary artery into the LAA and/or a conduit drawing blood from the LAA by a Bernoulli effect. In one embodiment, a method comprises implanting a conduit in a pulmonary vein, expanding an inlet portion such that the conduit becomes anchored within the vein and directs blood through an outlet portion of the conduit into or toward the left atrial appendage.

20 Claims, 28 Drawing Sheets

Related U.S. Application Data continuation-in-part of application No. 14/220,929, filed on Mar. 20, 2014, now Pat. No. 9,089,414.

(60) Provisional application No. 61/804,518, filed on Mar. 22, 2013.

(51) Int. Cl.
| | | |
|---|---|---|
| *A61F 2/844* | (2013.01) | |
| *A61F 2/848* | (2013.01) | |
| *A61F 2/915* | (2013.01) | |
| *A61F 2/07* | (2013.01) | |
| *A61F 2/89* | (2013.01) | |
| *A61F 2/966* | (2013.01) | |
| *A61F 2/82* | (2013.01) | |
| *A61F 2/24* | (2006.01) | |
| *A61F 2/06* | (2013.01) | |

(52) U.S. Cl.
CPC ............... *A61F 2/89* (2013.01); *A61F 2/915* (2013.01); *A61F 2/966* (2013.01); *A61F 2/24* (2013.01); *A61F 2002/068* (2013.01); *A61F 2002/821* (2013.01); *A61F 2002/8483* (2013.01); *A61F 2250/0039* (2013.01)

(58) Field of Classification Search
CPC .... A61F 2/89; A61F 2/91; A61F 2/915; A61F 2/966; A61F 2002/0039; A61F 2002/068; A61F 2002/821; A61F 2002/8483; A61F 2230/0069; A61F 2250/0039; A61B 17/0057; A61B 17/11; A61B 17/12122; A61B 17/12172; A61B 2017/00243; A61M 27/002; A61M 2210/125

See application file for complete search history.

(56) References Cited

U.S. PATENT DOCUMENTS

| | | | |
|---|---|---|---|
| 8,097,015 | B2 | 1/2012 | Devellian |
| 2002/0026233 | A1 | 2/2002 | Shaknovich |
| 2003/0023266 | A1 | 1/2003 | Borillo et al. |
| 2005/0222533 | A1* | 10/2005 | Chanduszko .... A61B 17/00234 604/8 |
| 2005/0234540 | A1* | 10/2005 | Peavey ............ A61B 17/12022 623/1.18 |
| 2008/0039879 | A1 | 2/2008 | Chin et al. |
| 2008/0249397 | A1 | 10/2008 | Kapadia |
| 2009/0163847 | A1 | 6/2009 | Kapadia |
| 2011/0082465 | A1 | 4/2011 | Verma |
| 2011/0208233 | A1 | 8/2011 | McGuckin, Jr. et al. |
| 2011/0276075 | A1 | 11/2011 | Fung et al. |
| 2011/0313283 | A1 | 12/2011 | Kapadia |
| 2012/0022427 | A1 | 1/2012 | Kapadia |
| 2012/0065652 | A1 | 3/2012 | Cully et al. |
| 2012/0065662 | A1 | 3/2012 | van der Burg et al. |
| 2012/0157916 | A1 | 6/2012 | Quinn et al. |
| 2012/0239083 | A1 | 9/2012 | Kreidler |
| 2013/0012982 | A1 | 1/2013 | Khairkhahan et al. |
| 2014/0228733 | A1 | 8/2014 | Martinez et al. |

FOREIGN PATENT DOCUMENTS

| | | |
|---|---|---|
| CN | 101252894 A | 8/2008 |
| CN | 101309651 A | 11/2008 |
| CN | 102510735 A | 6/2012 |
| EP | 2158866 A1 | 3/2010 |

OTHER PUBLICATIONS

CN Office Action issued for Application No. 201480017071.0, dated Mar. 3, 2016.

Yao Jing etc., "Research progress of percutaneous closure of the left atrial appendage to prevent thromboembolism in patients with atrial fibrillation"; Chinese Journal of Interventional Cardiology, vol. 19, issue 3, Jun. 30, 2011, pp. 172-174.

European Supplementary Search Report for EP14768187.8, dated Jul. 25, 2016.

CN Office Action issued for Application No. 201480017071.0 dated Oct. 20, 2016.

* cited by examiner

DEVICE AND METHOD FOR INCREASING FLOW THROUGH THE LEFT ATRIAL APPENDAGE

FIELD

The present invention relates to devices and methods for increasing flow through the left atrial appendage of the human heart, thereby helping to protect against flow stagnation in the left atrial appendage.

BACKGROUND

Cardiac Arrhythmias are abnormal heart rhythms that can cause the heart to pump blood less effectively. Atrial fibrillation (AF) is one of the most common heart arrhythmia conditions. AF causes the left atrium to beat irregularly and reduces the efficiency of the "atrial kick" that helps to move blood into the left ventricle. The left atrial appendage (LAA) is a muscular pouch located high on the free wall of the left atrium. The anatomy of the LAA is such that blood has a tendency to stagnate and form clots within the LAA. As blood flow is reduced with the progression of AF, the potential for clot formation increases tremendously. Clots formed in the LAA can embolize into the bloodstream and move into the brain, where they can become lodged and eventually lead to stroke.

Existing techniques to prevent flow stagnation in the LAA include occlusion of the LAA as in U.S. Pat. No. 6,730,108 to Van Tassel, remodeling or dilation of the LAA to increase blood flow as in U.S. Patent Application Publication No. 2005/0234540 A1 (Peavey et al.), and piercing the LAA for placement of conduits to increase blood flow as in U.S. Pat. No. 8,019,404 to Kapadia and U.S. Patent Application Publication No. 2012/0022427 A1 (Kapadia). Occluding the LAA is undesirable for a variety of reasons, for example, because the LAA is a source of important hormones, and because the geometry of the LAA varies from person to person, making occlusion of the oval-shaped ostium with an implant difficult. Also, known occlusion devices typically are mounted or secured to tissue surrounding the LAA. Since the tissue surrounding the LAA is relatively thin, implanting such an occlusion device can increase the risk of rupture and pericardial effusion. Additionally, it is believed that the LAA acts as a compliance chamber and helps to regulate blood pressure in the left atrium. Hence, it is desirable to maintain the flow of blood through the LAA.

Similarly, simply remodeling or dilating the LAA in cases of AF is ineffective in preventing flow stagnation because the lack of atrial contraction still limits the amount of blood flowing through the LAA. Accordingly, improvements to devices and methods for increasing flow through the LAA are desirable.

SUMMARY

Several embodiments of devices and methods shown and described herein are directed to increasing blood flow through the left atrial appendage. In one representative embodiment, a method for implanting a prosthetic conduit into a cardiac structure comprises inserting a distal end of a delivery catheter into the left atrium of the heart, the conduit being carried in a radially compressed or collapsed state by the distal end portion of the delivery apparatus. The method further comprises expanding an inlet portion of the conduit in a pulmonary vein such that the inlet portion of the conduit becomes anchored within the pulmonary vein and directs a flow of blood from the pulmonary vein through a lumen of the conduit and outwardly through an outlet portion of the conduit. The outlet portion of the conduit is located such that the flow of blood is directed substantially into or toward the left atrial appendage.

Another representative embodiment of a method for implanting a conduit in the heart comprises anchoring an inlet portion of the conduit within a pulmonary vein such that the conduit extends from the pulmonary vein into the left atrium and directs a flow of blood from the pulmonary vein through a lumen of the conduit and outwardly through an outlet portion of the conduit in a direction substantially toward the left atrial appendage.

Another representative embodiment of a method for implanting a conduit in the heart comprises inserting a distal end portion of a delivery catheter into the left atrium of the heart, the conduit being carried in a radially compressed or collapsed state by the distal end portion of the delivery apparatus. The inlet portion of the conduit is expanded in the left atrial appendage such that the inlet portion of the conduit becomes anchored within the left atrial appendage and directs blood in the left atrial appendage to flow through a lumen of the conduit and outwardly through an outlet portion of the conduit. The outlet portion is located such that the flow of blood from the outlet portion is directed to flow in a direction toward the mitral valve.

In another representative embodiment, a prosthetic conduit configured to be implanted into a cardiac structure comprises a radially collapsible and expandable tubular body defining a lumen. The tubular body can include an inlet portion and an outlet portion, and the inlet portion can be configured to be located in a pulmonary vein. The prosthetic conduit can be configured to direct a flow of blood from the pulmonary vein through the lumen of the prosthetic conduit and outwardly through the outlet portion in a direction toward the left atrial appendage.

In another representative embodiment, a prosthetic conduit configured to be implanted into a cardiac structure comprises a radially collapsible and expandable tubular body defining a lumen. The tubular body can include an inlet portion and an outlet portion, and the inlet portion can be configured to be located in the left atrial appendage. The inlet portion can be permeable to blood, and the prosthetic conduit can be configured to direct a flow of blood from the left atrial appendage in a direction toward the mitral valve.

The foregoing and other objects, features, and advantages will become more apparent from the following detailed description, which proceeds with reference to the accompanying figures.

DETAILED DESCRIPTION

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties, or groups described in conjunction with a particular aspect, embodiment, or example are to be understood to be applicable to any other aspect, embodiment, or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel feature, or any novel combination of features disclosed in this specification (including any accompanying claims, abstract, and drawings), or to any novel step, or any novel combination of steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B", "C", "A and B", "A and C", "B and C", or "A, B, and C".

As used herein, the term "coupled" generally means physically coupled or linked and does not exclude the presence of intermediate elements between the coupled items absent specific contrary language.

Figure 1A:
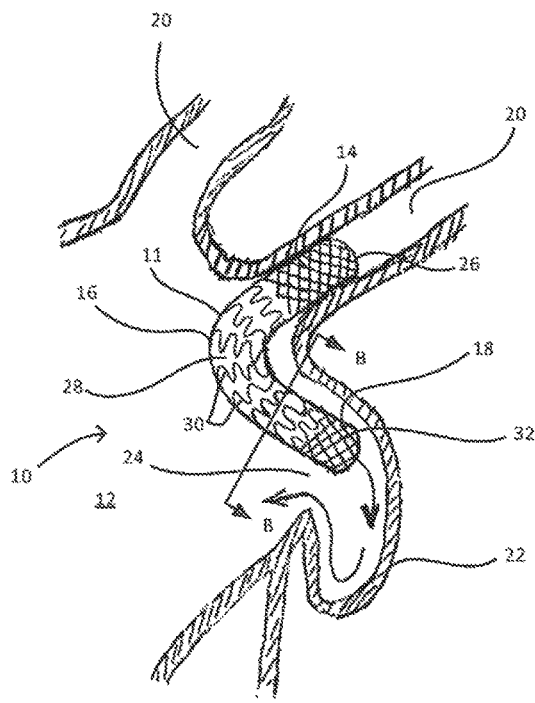
FIG. 1A is a partial cross-sectional view of the left atrium of a human heart showing an exemplary embodiment of a conduit anchored in a pulmonary vein and oriented to direct a flow of blood into the LAA.

Referring to FIG. 1A, there is shown a prosthetic heart implant in the form of a conduit 10, according to one embodiment, in a partial cross-section of a left atrium 12 of a human heart. The conduit 10 comprises a generally tubular body or sleeve 11 defining a lumen 13 (FIGS. 1B and 1C) and including an inlet portion 14, an elbow portion 16, and an outlet portion 18. The inlet portion 14 is configured to be located in a pulmonary vein 20. The conduit 10 comprises a substantially curved shape that curves along its length such that the outlet portion 18 is oriented in or substantially toward a left atrial appendage (LAA) 22 when the conduit 10 is deployed in the body. The conduit 10 is configured to utilize the pressure differential between the pulmonary vein 20 and the LAA 22 to increase the blood flow through the LAA 22. In this manner, the conduit 10 can direct higher-pressure blood from the pulmonary vein 20 to flow through the lumen 13 into the ostium 24 of the LAA 22, where the blood pressure is lower, thereby increasing the flow velocity and/or the flow rate into and out of the LAA 22. Increased flow velocity through the LAA 22 can act to minimize or prevent flow stagnation and thrombus formation in patients with Atrial Fibrillation (AF). As depicted in the illustrated embodiment, the conduit 10 can be sized such that the outlet portion 18 extends through the ostium 24 into the LAA 22 to maximize blood flow into and through the LAA 22. In alternative embodiments, the conduit 10 can be sized such that the outlet portion 18 directs blood to flow into the LAA 22 but the outlet portion itself does not extend into the LAA 22.

The inlet portion 14 can comprise a substantially rigid zone for anchoring the conduit 10 in a pulmonary vein 20. The inlet portion 14 can comprise, for example, a radially expandable metal inlet frame or stent 26, similar to a coronary stent or a stent used in an expandable transcatheter heart valve or an aortic stent graft. Similar to known stents, the inlet frame 26 can have a mesh-like configuration or can be formed from a plurality of angled struts allowing radial compression and expansion of the inlet frame 26.

When placed into the pulmonary vein 20, the inlet frame 26 of the inlet portion 14 can be radially expanded against the walls of the pulmonary vein 20 to hold the conduit 10 in place. Generally, the inlet portion 14 expands to fill the entire ostium of the pulmonary vein 20, thereby diverting the entirety of the blood flow from that vein. However, alternatively, the inlet portion 14 can be shaped to occupy only a portion of the ostium of the pulmonary vein 20 when expanded, thereby diverting only a portion of the blood flow. The inlet frame 26 of the inlet portion 14 can be fabricated from a biocompatible metal, and can be covered on the outer and/or inner surface with a flexible sleeve or covering 28, such as a woven or non-woven sheet. The sheet can be formed from a polymeric material such as polytetrafluoroethylene (PTFE, for example, ePTFE), polyethylene terephthalate (PET), silicone, extruded polyurethane, silicone-polyurethane, polycarbonate urethane (PCU), etc.

The inlet frame 26 can be made of any of various suitable plastically-expandable materials (e.g., stainless steel, etc.) or self-expanding materials (e.g., Nitinol) as known in the art. When constructed of a plastically-expandable material, the inlet frame 26 (and thus the conduit 10) can be crimped to a radially compressed or collapsed state on a delivery catheter and then expanded inside a patient by an inflatable balloon or by an equivalent expansion mechanism. When constructed of a self-expandable material, the inlet frame 26 (and thus the conduit 10) can be crimped to a radially collapsed state and restrained in the collapsed state by insertion into a sheath or equivalent mechanism of a delivery catheter. Once inside the body, the conduit can be advanced from the delivery sheath, which allows the inlet frame 26 to expand to its functional size.

Figure 1B:
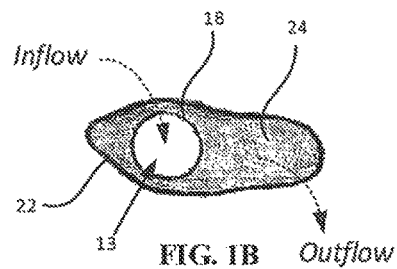
FIG. 1B is a cross-sectional view taken substantially along line B-B of FIG. 1A showing the conduit of FIG. 1A located in the ostium of the LAA.
Figure 1C:
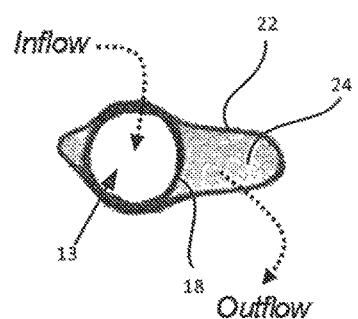
FIG. 1C is a cross-sectional view taken substantially along line B-B of FIG. 1A showing an alternative embodiment of the conduit of FIG. 1A located in the ostium of the LAA.
Figure 1D:
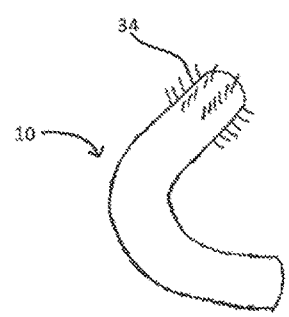
FIG. 1D is a perspective view of a conduit having barbs.

In alternative embodiments, the inlet portion 14 can comprise hooks or barbs 34 disposed around the exterior of the inlet portion 14, as shown in FIG. 1D (features such as inlet and outlet frames 26, 32, and annular hoops 30 are omitted for clarity). In this manner, the barbs 34 can engage the tissue surrounding the inlet portion 14, thereby holding the conduit 10 in place. It should be understood that barbs such as the barbs 34 can be used in combination with any of the embodiments described herein. In still other alternative embodiments, the conduit 10 can have a sufficiently narrow diameter such that radially collapsing the conduit 10 for delivery is not required.

The elbow portion 16 comprises a substantially flexible zone capable of being shaped or bent so as to point or direct the outlet portion 18 substantially in the direction of or into the LAA 22. In particular embodiments, for example, the elbow portion 16 is shape-set in the manufacturing process to assume the curved shape shown in FIG. 1A when released from a delivery sheath. In particular embodiments, the conduit 10 can be radially compressed and loaded into the sheath of a delivery apparatus. The sheath retains the conduit 10 in a radially compressed and straightened configuration. When released from the sheath, the conduit 10 expands and assumes the curved shape shown in FIG. 1A. The elbow portion 16 can comprise, for example, a plurality of longitudinally spaced apart annular metal hoops 30, which can be secured to and covered by the covering 28. Each of the hoops 30 can have a sinusoidal or undulating shape to promote crimping of the elbow portion 16 to a collapsed state for delivery into the patient. Alternatively, the support structure can be disposed helically along the conduit axis.

The outlet portion 18 can comprise a substantially rigid zone, and can comprise, for example, a radially compressible and expandable outlet frame 32 secured to and covered by the covering 28. The outlet frame 32 can have a similar configuration to the inlet frame 26 in the inlet portion 14. In some embodiments, the outlet portion 18 is sized such that it does not necessarily contact the surrounding tissue of the ostium 24 of the LAA 22, in which case the elbow portion 16 exhibits sufficient rigidity, once implanted, to retain its curved shape while directing blood flow directly at the LAA 22. FIG. 1B is a cross-section taken substantially along line B-B of FIG. 1A. As shown in FIG. 1B, the outlet portion 18 does not occlude the ostium 24. Therefore, blood can flow into the LAA 22 via the outlet portion 18, and can flow out of the LAA 22 via the gap or space between the outer surface of the outlet portion 18 and the surrounding tissue of the ostium 24.

In other embodiments, the outlet portion 18 can be sized to contact the surrounding tissue of the ostium 24 and/or the LAA 22 but does not otherwise fully occlude the ostium 24. As shown in FIG. 1C, for example, the outlet portion 18 expands to immobilize the conduit 10 in the LAA 22 by contacting one or more portions of the ostium 24, such as portions of the ostium that are about 180° apart as depicted in FIG. 1C, while leaving a portion of the ostium 24 open on either side of the outlet portion 18 to allow blood to flow out of the LAA 22 around the conduit 10.

In the embodiment shown, the inlet portion 14 is placed into the pulmonary vein 20 closest in proximity to the ostium 24 of the LAA 22. However, in other embodiments, the inlet portion 14 can be placed into any of the four pulmonary veins that enter the left atrium 12. It should be noted that any of the embodiments described herein can be deployed in any of the four pulmonary veins. Additionally, although shown in the context of minimizing or preventing flow stagnation in the LAA 22, the conduit 10, as well as other embodiments of conduits described herein, are generally applicable to problems of flow stagnation in other parts of the body, including in other cardiac structures.

In particular embodiments, the inlet frame 26, the outlet frame 32 and the intermediate rings 30 can all made of a self-expanding material such as Nitinol, and the entire conduit 10 can be radially compressed or collapsed and retained in a delivery sheath for delivery into the patient. In other embodiments, these components can be made of a plastically-expandable material and the entire conduit 10 can be radially compressed or collapsed on to a delivery catheter and expanded inside the heart using a balloon of the delivery catheter or equivalent expansion mechanism. For example, suitable plastically-expandable materials that can be used to form the inlet and outlet frames 26, 32 include, without limitation, stainless steel, a nickel based alloy (e.g., a nickel-cobalt-chromium alloy), polymers, or combinations thereof. In particular embodiments, the inlet and outlet frames 26, 32 can be made of a nickel-cobalt-chromium-molybdenum alloy, such as MP35N® alloy (SPS Technologies, Jenkintown, Pa.), which is equivalent to UNS R30035 alloy (covered by ASTM F562-02). MP35N®/UNS R30035 alloy comprises 35% nickel, 35% cobalt, 20% chromium, and 10% molybdenum, by weight.

The covering 28 can be a woven fabric sheet of material (e.g., PET) that extends over the inlet and outlet frames 26, 32, and the intermediate rings 30. The inlet and outlet frames 26, 32, and the intermediate rings 30 can be sutured or otherwise secured to the covering 28. In other embodiments, the covering 28 can be an internal sleeve and the inlet and outlet frames 26, 32, and the intermediate rings 30 can be sutured or otherwise secured to the outside of the covering 28. In other embodiments, the covering 28 can extend externally and internally over the inlet and outlet frames 26, 32 and the intermediate rings 30 such that the inlet and outlet frames 26, 32 and intermediate rings 30 are disposed between the internal and external woven sheets. In still other embodiments, the covering 28 can be formed from a non-woven polymeric material. For example, the covering 28 can be a thermoset or thermoplastic material (e.g., urethane) that is molded to have the desired functional shape. In some embodiments, the inlet and outlet frames 26, 32, and the intermediate rings 30 can be molded in or partially within the covering 28 during the molding process.

In the illustrated embodiment, the covering 28 extends continuously from the very end of the inlet portion 14 of the conduit 10 to the very end of the outlet portion 18 of the conduit 10. In other embodiments, however, one or more portions of the conduit 10 can remain uncovered by the covering 28. For example, the inlet frame 26 can include an uncovered portion because it is anchored within the pulmonary vein 20. In other embodiments described below, portions of the conduit 10 can be uncovered to allow blood to flow through openings in the conduit 10.

Figure 2:
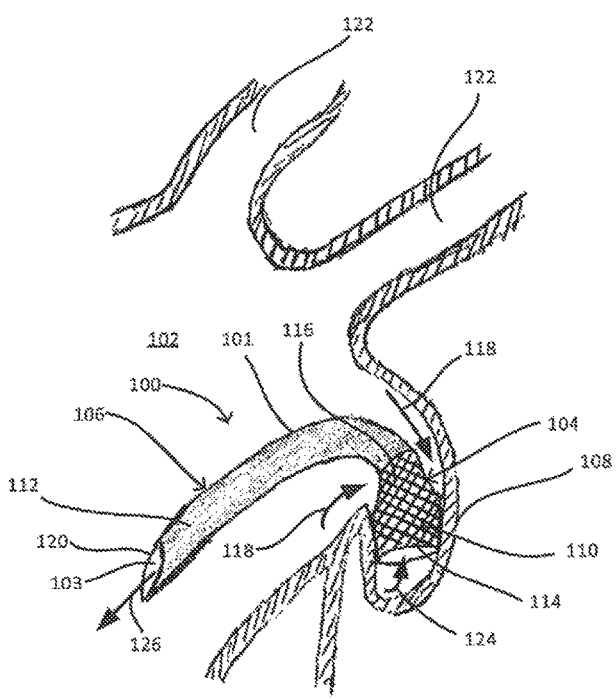
FIG. 2 is a partial cross-sectional view of the left atrium of a human heart showing another embodiment of a conduit anchored in the LAA and configured to direct a flow of blood out of the LAA.

Referring to FIG. 2, there is shown another embodiment of a conduit 100 in a partial cross-section of a left atrium 102 of a human heart. The conduit 100 comprises a generally tubular body or sleeve 101 defining a lumen 103 and including an inlet portion 104 and an outlet portion 106. The inlet portion 104 is configured to be placed into a LAA 108 to promote the outward flow of blood from the LAA 108 through the lumen 103 into the left atrium 102, thereby helping to protect against flow stagnation and thrombus formation. The inlet portion 104 comprises an expandable inlet stent or frame 110, which is connected to a sleeve 112 that directs blood from the LAA 108 to flow towards the mitral valve (not shown). The inlet frame 110 in the illustrated configuration has an enlarged inflow portion 114 and a tapered outflow portion 116 of a reduced diameter extending outwardly from the LAA 108 into the left atrium 102. When expanded, the inflow portion 114 can anchor the conduit 100 in place against the surrounding tissue within the LAA 108.

At least the outflow portion 116 of the inlet frame 110 is uncovered so that blood in the left atrium 102 can flow into the LAA 108 via the openings in the outflow portion 116 of the inlet frame 110, in the direction indicated by arrows 118. The tapered shape of the outflow portion 116 can ensure adequate blood flow into the LAA 108 through or around the inlet frame 110. Generally, the inflow portion 114 does not occupy the entire ostium of the LAA 108, but rather expands to contact the walls of the LAA 108 at locations about 180° apart in a manner similar to the conduit of FIG. 1C.

However, the inflow portion 114 can be configured to expand within the LAA 108 such that it occupies the entire ostium of the LAA 108, or substantially the entire ostium, as long as blood can flow into the LAA 108 via the uncovered portions of the inlet frame 110. In an alternative embodiment, the entire extent of the inlet frame 110 can be covered by the sleeve 112, as long as the inlet frame 110 does not occlude the entire ostium and permits sufficient blood flow into the LAA 108 between the outer surface of the inlet frame 110 and the ostium.

The sleeve 112 comprises a hollow tube having an outlet 120 pointed in the direction of the mitral valve (not shown). Blood flowing from the pulmonary veins 122 and the left atrium 102 toward the mitral valve during diastole, as well as opening of the leaflets of the mitral valve and expansion of the left ventricle, induces a Bernoulli-type effect in the vicinity of the outlet 120. This establishes a pressure differential between the left atrium 102 and the LAA 108, with the pressure near the outlet 120 being lower than the pressure near the LAA 108. This pressure differential, in turn, causes blood to be drawn from the LAA 108 into the conduit 100 in the direction indicated by arrow 124, and to flow out of the conduit 100 generally toward the mitral valve in a direction indicated by arrow 126.

The sleeve 112 generally comprises a tube fabricated from a polymeric material such as PTFE. However, any suitable biocompatible material may be used. The sleeve 112 desirably is shape set to have a predetermined curvature as shown to direct the flow of blood from the LAA 108 towards the mitral valve. In particular embodiments, the conduit 100 can be radially compressed and loaded into the sheath of a delivery apparatus. The sheath retains the conduit 100 in a radially compressed and straightened configuration. When released from the sheath, the conduit 100 expands and assumes the curved shape shown in FIG. 2.

The sleeve 112 as depicted in FIG. 2 does not include any metal supports (e.g., stents or rings) but can include such supports to increase the strength of the sleeve 112 and/or to ensure the sleeve remains in an open configuration throughout its length once implanted. Although shown in the context of increasing blood flow through the LAA 108, the conduit 100 is generally applicable to problems of flow stagnation in other parts of the body, including in other cardiac structures.

Figure 3:
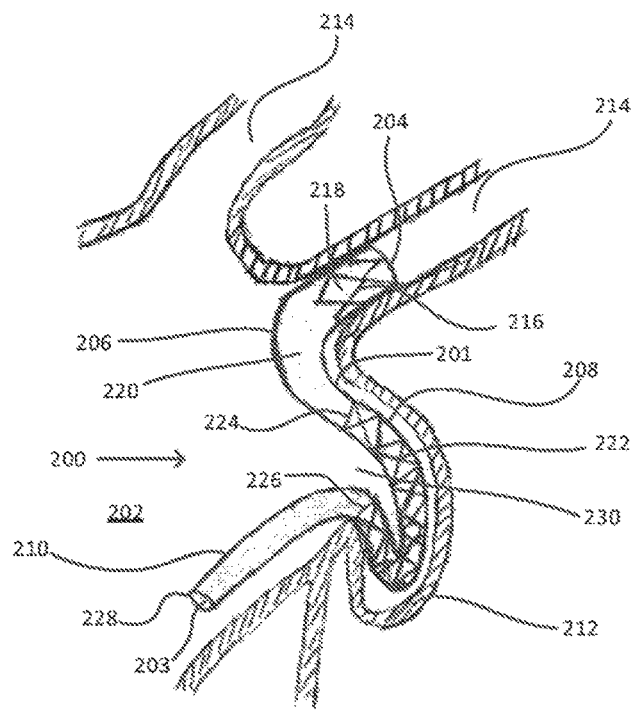
FIG. 3 is a partial cross-sectional view of a left atrium of a human heart showing another embodiment of a conduit anchored in a pulmonary vein and including an intermediate portion configured to be located in the LAA.

Referring now to FIG. 3, there is shown another embodiment of a conduit 200 in a partial cross-section of a left atrium 202 of a human heart. The conduit 200 comprises a generally tubular body or sleeve 201 defining a lumen 203 and including an inlet portion 204, an elbow portion 206, an uncovered intermediate portion 208, and an outlet portion 210. The conduit 200 is configured to help protect against flow stagnation in a LAA 212 by directing higher-pressure blood flow from a pulmonary vein 214 into the LAA 212, where the blood pressure is lower. The uncovered portion 208 is configured to promote an increase in blood flow through the LAA by simultaneously allowing blood to enter the LAA via the elbow portion 206 and promoting the outflow of blood from the LAA via Bernoulli-type action at the outlet portion 210.

The inlet portion 204 can comprise a substantially rigid zone for anchoring the conduit 200 in the pulmonary vein 214. The inlet portion 204 can comprise, for example, a radially compressible and expandable metal inlet frame or stent 216, as already described. When placed into the pulmonary vein 214, the inlet frame 216 of the inlet portion 204 can be radially expanded against the walls of the pulmonary vein 214 to hold the conduit 200 in place. Generally, the inlet portion 204 expands to fill the entire ostium of the pulmonary vein 214, thereby diverting the entirety of the blood flow from that vein. However, alternatively, the inlet portion 204 can be shaped to occupy only a portion of the ostium of the pulmonary vein 214 when expanded, thereby diverting only a portion of the blood flow. The inlet frame 216 of the inlet portion 204 can be fabricated from a biocompatible metal, and can be covered with a flexible sleeve, or cover 218, such as a woven or non-woven sheet formed from a polymeric material such as PTFE or PET.

The elbow portion 206 can comprise a substantially flexible zone capable of being shaped or bent so as to promote the placement of the uncovered intermediate portion 208 within the LAA 212. In particular embodiments, for example, the elbow portion 206 is shape set in the manufacturing process to assume the curved shape shown in FIG. 3 when released from a delivery sheath. The elbow portion 206 can comprise, for example, a hollow tube or sleeve 220 in communication with the inlet portion 204 at one end of the sleeve 220 and uncovered intermediate portion 208. The tube, or sleeve, 220 of the elbow portion 206 can be an extension of the covering 218 of the inlet frame 216 (e.g., the sleeve 218 and the sleeve 220 can be a single sleeve), and can comprise a flexible polymeric material such as PTFE. The elbow portion 206 as depicted in FIG. 3 does not include any metal supports (e.g., stents or rings) but can include such supports to increase the strength of the elbow portion 206 and/or to ensure the elbow portion 206 remains in an open configuration throughout its length once implanted. In this manner, the elbow portion 206 directs blood flow from the inlet portion 204 into the uncovered portion 208 and thereby into the LAA 212.

The uncovered intermediate portion 208 can comprise a flexible open structure 222, such as a metal stent or frame, in fluidic communication with the elbow portion 206 via an outlet 224 of the elbow portion 206. The intermediate portion 208 can also be in fluidic communication with the outlet portion 210 via an inlet 226 of the outlet portion 210. In the embodiment shown, the uncovered intermediate portion 208 follows a generally serpentine path that substantially conforms to the interior contours of the LAA 212. Higher-pressure blood from the pulmonary vein 214 enters the uncovered intermediate portion 208 via the outlet 224 of the elbow portion 206 and is allowed to flow freely through the flexible open structure 222 to circulate throughout the LAA 212. Blood can then either reenter the uncovered intermediate portion 208 due to a pressure differential between the inlet 226 of the outlet portion 210 and the outlet 228 of the outlet portion 210, as further discussed below, or flow directly into the left atrium 202 by exiting through the ostium 230 around the conduit 200. Alternatively, the uncovered intermediate portion 208 need not follow a serpentine path within the LAA 212, but may comprise any shape suitable for allowing blood to diffuse throughout the LAA 212.

The outlet portion 210 can comprise a hollow tube having an outlet 228 pointed generally in the direction of the mitral valve (not shown). As discussed above with respect to the conduit of FIG. 2, blood flowing from pulmonary veins 214 toward the mitral valve during diastole induces a Bernoulli-type effect at the outlet 228. This establishes a pressure differential in the left atrium 202 with the pressure near the outlet 228 being lower than the pressure near the inlet 226 of the outlet portion 210. This pressure differential in turn causes blood to be drawn into the outlet portion 210 via the inlet 226. The combination of higher-pressure flow into the LAA 212 from pulmonary vein 214 via the uncovered intermediate portion 208 and outflow through outlet portion 210 via Bernoulli-type flow induction promotes increased blood flow into and out of the LAA 212, thereby helping to protect against flow stagnation and the formation of thrombi.

The outlet portion 210 generally comprises a tube fabricated from a polymeric material such as PTFE. However, any suitable biocompatible material may be used. The outlet portion 210 desirably is shape set to have a predetermined curvature, as shown, to direct the flow of blood from the LAA 212 towards the mitral valve. The outlet portion 210 as depicted in FIG. 3 does not include any metal supports (e.g., stents or rings) but can include such supports to increase the strength of the tube and/or to ensure the tube remains in an open configuration throughout its length once implanted. In alternative embodiments, the diameter of the outlet portion 210 can be less than the diameter of the uncovered intermediate portion 208, thereby increasing the pressure within the outlet portion 210 and causing a greater proportion of the blood to flow out of the uncovered intermediate portion 208 and into the LAA 212. Additionally, although shown in the context of increasing blood flow through the LAA 212, the conduit 200 is generally applicable to problems of flow stagnation in other parts of the body, including in other cardiac structures.

Figure 4:
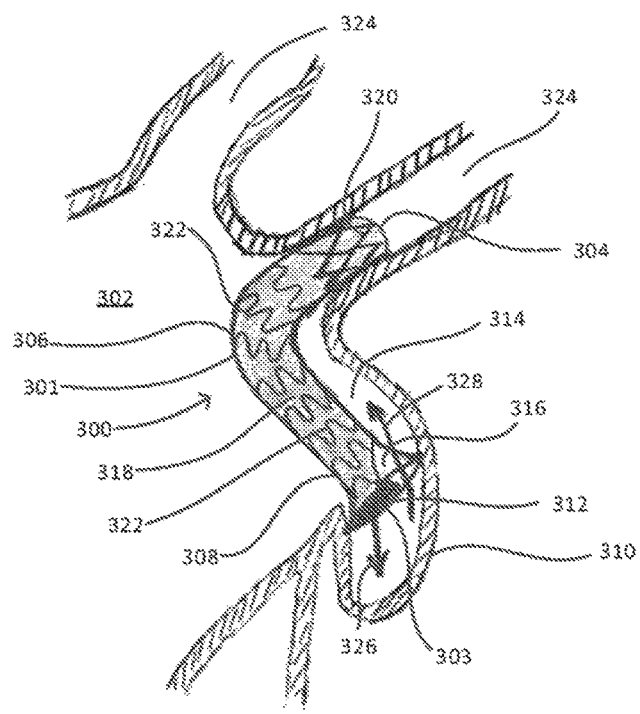
FIG. 4 is a partial cross-sectional view of a left atrium of a human heart showing another embodiment of a conduit anchored in a pulmonary vein and including a distal end portion configured to be located in the LAA.

Referring now to FIG. 4, there is shown another embodiment of a conduit 300 in a partial cross-section of a left atrium 302 of a human heart. The conduit 300 comprises a generally tubular body 301 defining a lumen 303 and including an inlet portion 304 having an inlet stent or frame 320, an elbow portion 306 comprising one or more annular hoops 322, an outlet portion 308 comprising one or more annular hoops 322, and a covering or sleeve 318 extending over the inlet frame 320 and the hoops 322. The inlet portion 304 and the elbow portion 306 can have the same characteristics and construction as described with respect to those components of the embodiment of FIG. 1 above. The sleeve 318 can extend the entire length of the conduit 300 except for areas of the outlet portion 308 that can remain uncovered to promote flow out of the LAA 310, as described below.

The outlet portion 308 comprises a flared outlet 312 generally in the shape of the bell of a trumpet. In the embodiment shown, the outlet portion 308 does not occlude the entire ostium 314 of the LAA 310. Rather, the outlet portion 308 contacts the walls of the LAA 310 at points about 180° apart while leaving a portion of the ostium 314 open on both sides of the conduit 300 in a manner similar to the conduit of FIG. 1C. In this manner, the outlet portion 308 acts to restrain the conduit in the LAA 310. Additionally, the outlet 312 can comprise an uncovered portion 316, as shown. As shown in FIG. 4, blood from a pulmonary vein 324 enters the LAA 310 via the outlet 312 of outlet portion 308 in a manner indicated by flow line 326, and exits the LAA 310 either by flowing through the uncovered portion 316, as indicated by flow line 328, or by flowing outwardly through the space between the outlet 312 and the ostium 314. In other embodiments, the outlet portion 308 can be configured to occupy the entire ostium 314 of the LAA 310, thereby forcing blood to exit the LAA via the uncovered portion 316. In addition, the outlet 312 can include more than one uncovered section 316, which need not be at the upper portion of the outlet.

Figure 5:
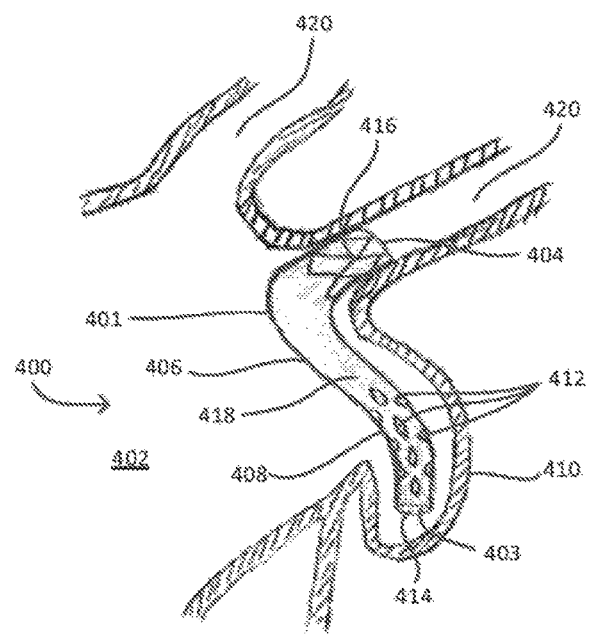
FIG. 5 is a partial cross-sectional view of a left atrium of a human heart showing another embodiment of a conduit anchored in a pulmonary vein and including a distal end portion defining a plurality of openings.

Referring now to FIG. 5, there is shown another embodiment of a conduit 400 in a partial cross-section of a left atrium 402 of a human heart. The conduit 400 comprises a generally tubular body 401 defining a lumen 403 and including an inlet portion 404 comprising an inlet stent or frame 416, an intermediate portion 406, and an outlet portion 408. The intermediate portion 406 can comprise a hollow tube fabricated from a polymeric material such as PTFE and oriented such that the outlet portion 408 is located substantially within a LAA 410. The outlet portion 408 is in communication with the intermediate portion 406, and can comprise a plurality of openings 412 in addition to an outlet 414 to allow blood from the pulmonary vein 420 to diffuse throughout the LAA 410 while minimizing the risk of obstruction of the blood flow in the conduit 400. In the embodiment shown, a single sleeve 418 covers the inlet frame 416 and forms the intermediate portion 406 and the outlet portion 408. However, alternatively, the intermediate portion 406, the outlet portion 408, and the sleeve 418 covering the inlet frame 416 can be separately fabricated and subsequently secured to each other to form an assembled unit.

Figure 6:
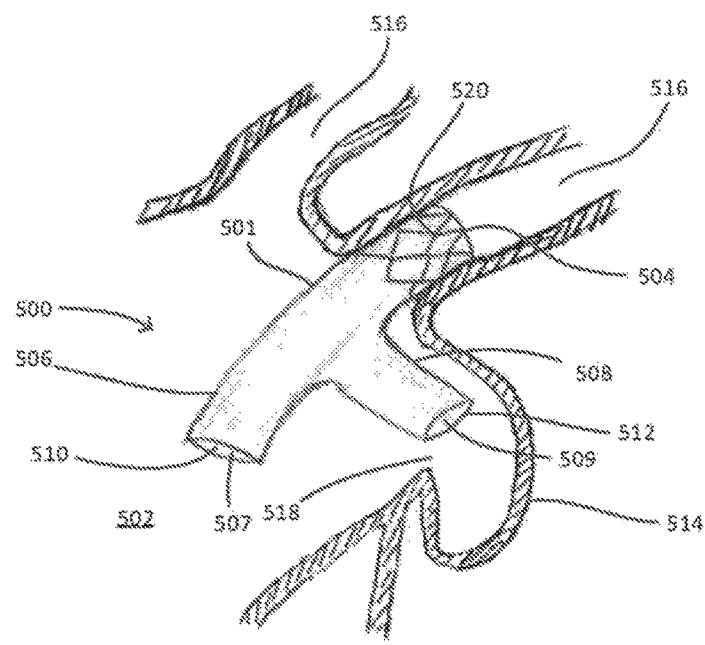
FIG. 6 is a partial cross-sectional view of a left atrium of a human heart showing another embodiment of a conduit anchored in a pulmonary vein and including an outlet portion and side branch portion.

Referring now to FIG. 6, there is shown another embodiment of a conduit 500 in a partial cross-section of a left atrium 502 of a human heart. The conduit 500 can comprise a generally tubular, T-shaped or Y-shaped body 501 including an inlet portion 504, an outlet portion 506 and a side branch portion 508. The inlet portion 504 can comprise an inlet stent or frame 520 for anchoring the inlet portion 504 in a pulmonary vein 516. The outlet portion 506 can comprise a hollow tube defining a lumen 507 in fluidic communication with inlet portion 504, and can be oriented such that a first outlet 510 points generally, for example, in the direction of the mitral valve (not shown), or generally in a direction away from the mitral valve, such as orthogonal to the mitral valve. The side branch portion 508 can also comprise a hollow tube defining a lumen 509 in communication with the inlet portion 504, and can be oriented such that a second outlet 512 points generally in the direction of a LAA 514. In this manner, blood flow from the pulmonary vein 516 can be redirected partially toward the LAA 514 and partially into the left atrium 502.

In the embodiment shown, the side branch portion 508 extends past the ostium 518 and into the LAA 514. However, in alternative embodiments, the side branch portion 508 can terminate outside the LAA without breaking the plane of the ostium 518 (e.g., the side branch portion 508 does not enter the LAA 514). The portions 506, 508 can comprise a polymeric material and can be integrally fabricated from a single piece of material, which can also extend over the inlet frame 520. The outlet and side branch portions 506, 508 as depicted in FIG. 6 do not include any metal supports (e.g., stents or rings) but can include such supports to increase the strength of the conduit and/or to ensure the conduit 500 remains in an open configuration throughout its length once implanted. In alternative embodiments, the conduit 500 can be configured such that the diameter of the outlet portion 506 and/or the side branch portion 508 can be adjusted to control the blood flow into the LAA 514.

Figure 7:
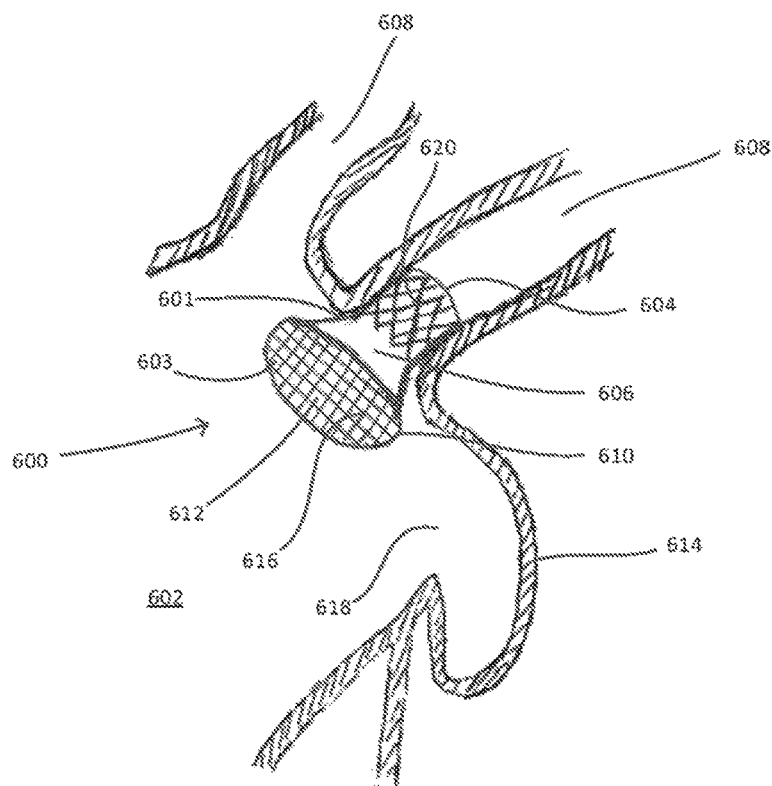
FIG. 7 is a partial cross-sectional view of a left atrium of a human heart showing another embodiment of a conduit having a flared outlet portion including a grating.

Referring now to FIG. 7, there is shown another embodiment of a conduit 600 in a partial cross-section of a left atrium 602 of a human heart. The conduit 600 comprises a generally tubular body or sleeve 601 defining a lumen 603 and including an inlet portion 604 and a flared outlet portion 606. However, in alternative embodiments, the outlet portion 606 need not be flared, but can comprise any suitable shape. The inlet portion 604 can be located in a pulmonary vein 608 and can include an inlet stent or frame 620 for anchoring the inlet portion 604 in the pulmonary vein 608, as described above. The outlet portion 606 can comprise an outlet 610 having a perforated or otherwise partially covered structure, such as a grating 612 (also referred to as a diffuser). The grating 612 promotes mixing, swirling, or turbulence in the blood flow exiting the outlet 610, which can increase the volume and velocity of flow into and/or out of the LAA 614. The grating 612 can include a plurality of panels, ridges, or vanes 616 oriented at various different angles to cause blood to flow in different directions as it exits the outlet 610. At least one of the vanes 616 of the grating 612 can be oriented so as to direct blood flow substantially in the direction of the ostium 618 of the LAA 614.

Figure 8:
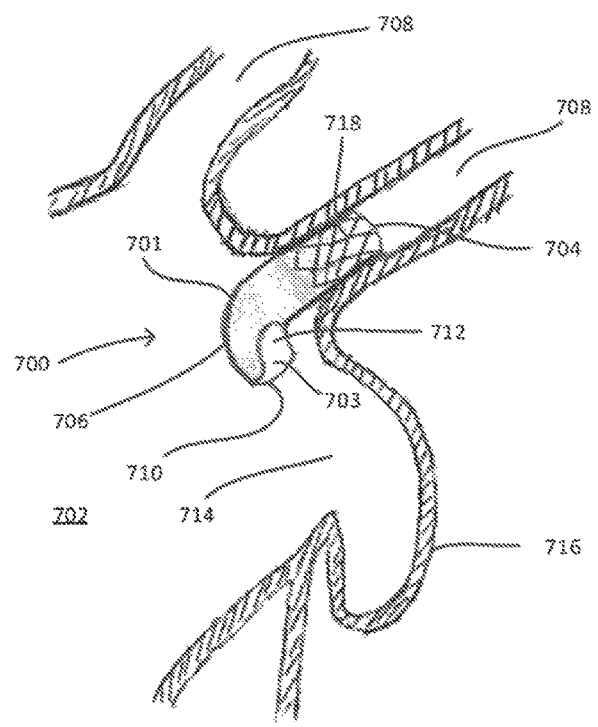
FIG. 8 is a partial cross-section view of a left atrium of a human heart showing another embodiment of a conduit having an outlet portion including a cutaway portion.

Referring now to FIG. 8, there is shown another embodiment of a conduit 700 in a partial cross-section of a left atrium 702 of a human heart. The conduit 700 comprises a generally tubular body or sleeve 701 defining a lumen 703 and including an inlet portion 704 and an outlet portion 706. The inlet portion 704 can be located in a pulmonary vein 708 and can comprise an inlet stent or frame 718 for anchoring the inlet portion 704 in the pulmonary vein 708, as described above. The outlet portion 706 can comprise an outlet section 710 having a cutaway portion 712, and can be oriented substantially in the direction of an ostium 714 of a LAA 716. The outlet portion 706 can comprise a substantially curved shape, which can be set during the manufacturing process or shaped during implantation of the conduit 700. The tubular body 701 can be fabricated from a polymeric material such as PTFE. In the embodiment shown, the outlet portion 706 does not break the plane of the ostium 714 of the LAA 716. However, in alternative embodiments, the outlet portion 706 may extend through the ostium 714 into the LAA 716 to promote increased blood flow.

Figure 9:
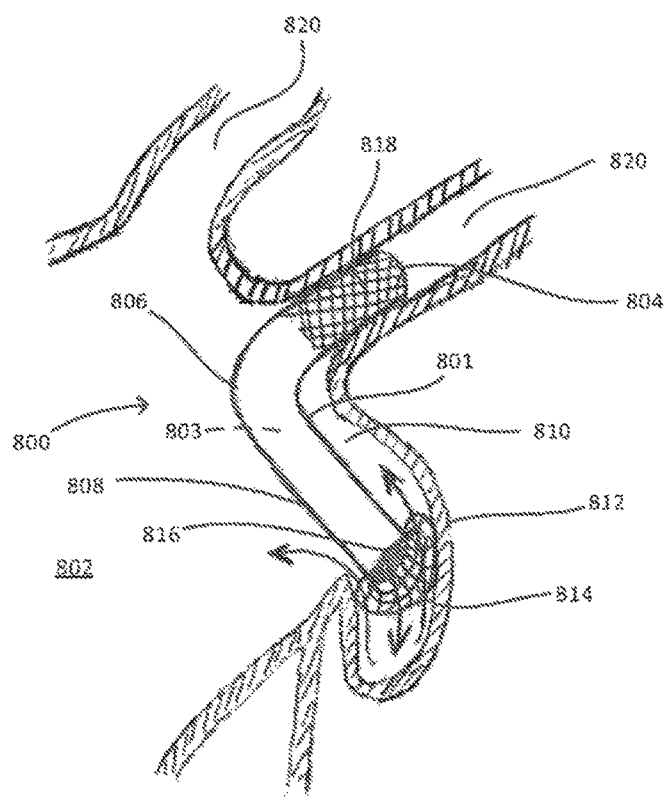
FIG. 9 is a partial cross-sectional view of a left atrium of a human heart showing another embodiment of a conduit anchored in a pulmonary vein and including a distal end portion having a mesh or cage.

Referring now FIG. 9, there is shown another embodiment of a conduit 800 in a partial cross-section of a left atrium 802 of a human heart. The conduit 800 comprises an elongated tubular body 801 defining a lumen 803 (indicated in phantom) and including an inlet portion 804, an elbow portion 806, and an outlet portion 808. The inlet portion 804 can include an inlet stent or frame 818 for anchoring the inlet portion 804 in a pulmonary vein 820, as described above. The outlet portion 808 extends through the ostium 810 of the LAA 812. Mounted to the outlet portion 808 is a mesh or cage 814 extending radially outward from an outlet 816 of the outlet portion 808. The cage 814 can have an enlarged diameter or size relative to a diameter or size of the outlet portion, for example, in the shape of a sphere or a portion of a sphere having a diameter greater than the diameter of the outlet 816, thereby acting to keep the tissue of the interior LAA walls from blocking the outlet 816. Blood from the pulmonary vein 820 flows into the LAA 812 via the outlet 816 and exits the LAA by flowing through the mesh or cage 814 and outwardly through the ostium 810, as shown by the flow lines in FIG. 9. The cage 814 can also act to restrain the outlet portion 808 of the tubular body 801 in the LAA by expanding against the LAA walls. The elbow and outlet portions 806, 808 as depicted in FIG. 9 do not include any metal supports (e.g., stents or rings) but can include such supports to increase the strength of the conduit 800 and/or to ensure the conduit remains in an open configuration throughout its length once implanted.

The cage 814 can be fabricated from any of various suitable plastically-expandable materials or self-expanding materials as known in the art. When constructed of a plastically-expandable material, the cage 814 can be crimped to a radially compressed or collapsed state on a delivery catheter and then expanded inside the LAA 812 by an inflatable balloon or equivalent expansion mechanism. When constructed of a self-expandable material, the cage 814 can be crimped to a radially compressed or collapsed state and restrained in the collapsed state by insertion into a sheath or equivalent mechanism of a delivery catheter. Once inside the LAA 812, the cage 814 can expand to its functional size when it is advanced from the delivery sheath. Suitable plastically-expandable materials and self-expanding materials are discussed above with respect to the preceding embodiments.

Figure 10:
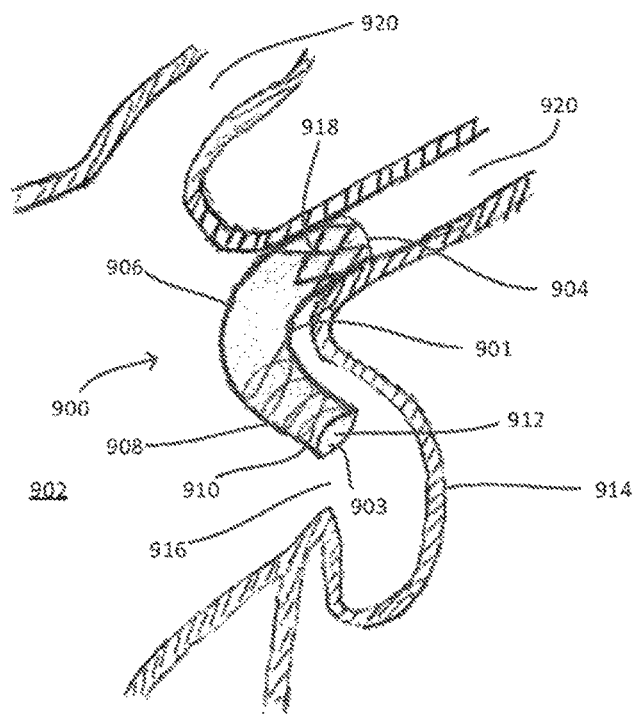
FIG. 10 is a partial cross-sectional view of a left atrium of a human heart showing another embodiment of a conduit anchored in a pulmonary vein including an outlet portion having a helical structure configured to induce vortices in the flow of blood.

Referring to FIG. 10, there is shown another embodiment of a conduit 900 in a partial cross-section of a left atrium 902 of a human heart. The conduit 900 comprises a generally tubular body or sleeve 901 defining a lumen 903 and including an inlet portion 904, an elbow portion 906, and an outlet portion 908. The inlet portion 904 can include an inlet stent or frame 918 for anchoring the inlet portion 904 in a pulmonary vein 920, as described above. The elbow portion 906 can comprise a hollow tube fabricated from a polymeric material such as PTFE. The outlet portion 908 can comprise a helical structure or otherwise tortuous path 910 in the interior of the outlet portion 908 to impart angular momentum and induce vortices in the flow of blood diverted from the pulmonary vein 920. As blood exits the outlet 912 into the LAA 914, the vortices and angular momentum imparted by the helical structure 910 can act to promote the flow of blood into a greater portion of the interior volume of the LAA 914, especially with respect to small crenellations within the trabeculae of the LAA. As depicted in FIG. 10, the outlet portion 908 is not located substantially within the LAA 914. However, in alternative embodiments, the outlet portion 908 can extend through the ostium 916 of the LAA into the interior of the LAA.

Figure 11:
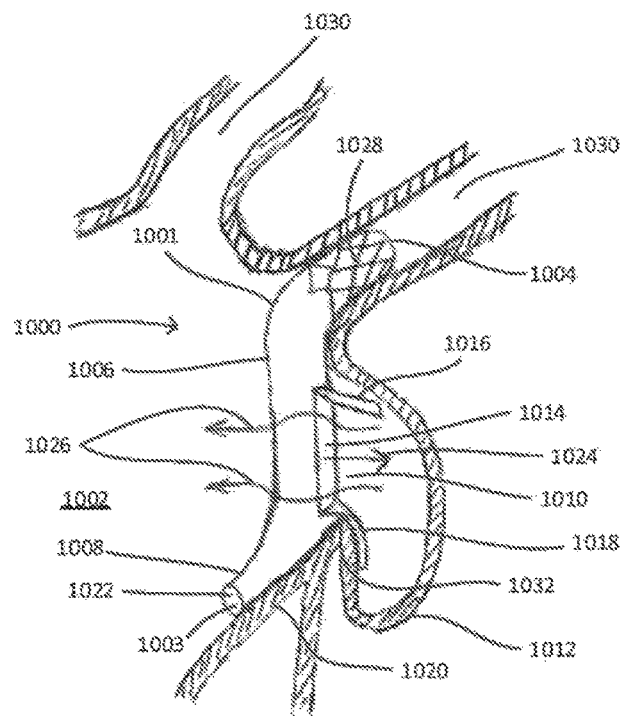
FIG. 11 is a partial cross-sectional view of a left atrium of a human heart showing another embodiment of a conduit anchored in a pulmonary vein and having an intermediate portion including an opening.

Referring to FIG. 11, there is shown another embodiment of a conduit 1000 in a partial cross-section of a left atrium 1002 of a human heart. The conduit 1000 comprises a generally tubular body 1001 defining a lumen 1003 and including an inlet portion 1004, an intermediate portion 1006, and outlet portion 1008. The inlet portion 1004 can comprise an inlet stent or frame 1028 for anchoring the inlet portion 1004 in a pulmonary vein 1030, as described above. The intermediate portion 1006 can comprise a hollow tube located substantially adjacent the ostium 1010 of the LAA 1012 and having an opening 1014 in communication with the ostium 1010 of the LAA 1012. The opening 1014 can be selectively opened and closed by upper and/or lower flaps 1016, 1018, which can open outwardly into the LAA. The lower flap 1018 can be configured to engage or grip the tissue 1032 of the interior of the LAA 1012, thereby helping to immobilize the outlet portion 1008 against the wall 1020 of the left atrium 1002, as shown in FIG. 11. Alternatively, the upper flap 1016 can be configured to engage or grip the tissue of the LAA 1012.

The outlet portion 1008 can comprise a substantially tapered shape wherein the diameter of the outlet 1022 is smaller than the diameter of the intermediate portion 1006. This acts to restrict the flow of blood out of the outlet 1022, thereby increasing the pressure within the lumen 1003 of the conduit 1000 and forcing a greater proportion of the blood to flow outwardly through the opening 1014 into the LAA 1012. Blood generally enters the LAA 1012 via the opening 1014 in the manner indicated by flow line 1024, and exits the LAA 1012 via the space between the ostium 1010 and the outer surface of the intermediate portion 1006 in the manner indicated by flow lines 1026. Because the diameter of the conduit 1000 is less than the overall width of the ostium 1010 of the LAA 1012, the conduit 1000 does not occlude the ostium 1010 and blood can freely flow out of the LAA 1012 around the conduit 1000 in the direction indicated by flow lines 1026.

Figure 12:
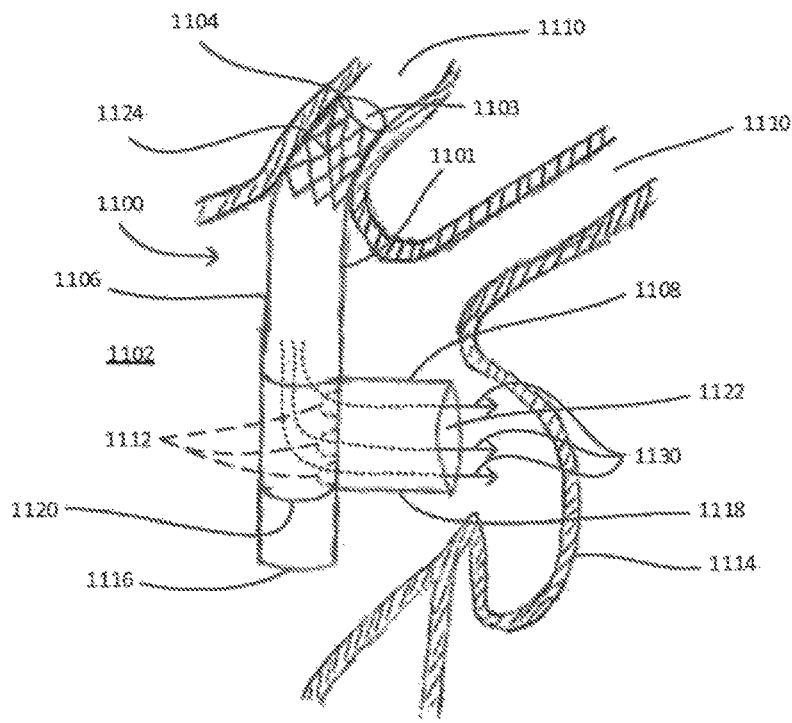
FIG. 12 is a partial cross-sectional view of a left atrium of a human heart showing another embodiment of a conduit anchored in a pulmonary vein and including a slidable attachment.

Referring to FIG. 12, there is shown another embodiment of a conduit 1100 in a partial cross-section of a left atrium 1102 of a human heart. The conduit 1100 comprises a generally tubular body 1101 defining a lumen 1103 and including an inlet portion 1104 and an outlet portion 1106. The conduit 1100 also comprises a slidable attachment or adjustable outlet portion, 1108. The inlet portion 1104 can be placed into a pulmonary vein 1110, and can comprise an inlet stent or frame 1124 for anchoring the inlet portion 1104 in the pulmonary vein 1110, as described above. The outlet portion 1106 can define a plurality of openings 1112 (shown in phantom) located along its length and oriented substantially in the direction of the LAA 1114. The terminus 1116 of the outlet portion 1106 can be substantially restricted, for example, comprising one or more small openings, or blocked to force blood to flow out of the plurality of openings 1112.

The slidable attachment 1108 can comprise a modular component having a first tube 1118 and a second tube 1120 in fluidic communication with one another, the longitudinal axes of the first and second tubes 1118, 1120 being substantially perpendicular to one another (e.g., in the illustrated embodiment, the longitudinal axis of the first tube 1118 is oriented horizontally and the longitudinal axis of the second tube 1120 is oriented vertically). The second tube 1120 of the slidable attachment 1108 can be configured to fit around and slidably engage the outlet portion 1106 of the conduit 1100 such that it can be moved along the length of the outlet portion 1106. In this manner, the slidable attachment 1108 can be positioned so as to point an outlet 1122 of the first tube 1118 substantially in the direction of the LAA 1114, and to enclose the plurality of openings 1112 to direct blood flow into the first tube 1118. Thus, blood from the pulmonary vein 1110 flows through outlet portion 1106, openings 1112, tubular portion 1118, and into the LAA 1114 in the direction of the flow lines 1130. Desirably, slidable attachment 1108 can be manufactured in a variety of sizes such that the appropriate size can be selected for use at the time of implantation. In alternative embodiments, the plurality of openings 1112 can be located anywhere along the length of the outlet portion 1106 or can extend along substantially the entire length of the outlet portion 1106. The openings 1112 corresponding to the desired location of the slidable attachment 1108 along the outlet portion 1106 can be uncovered to allow blood to flow into the slidable attachment 1108, while the remaining openings 1112 can be blocked or covered. Alternatively, the outlet portion 1106 may also comprise a single opening rather than a plurality of openings 1112.

Figure 13:
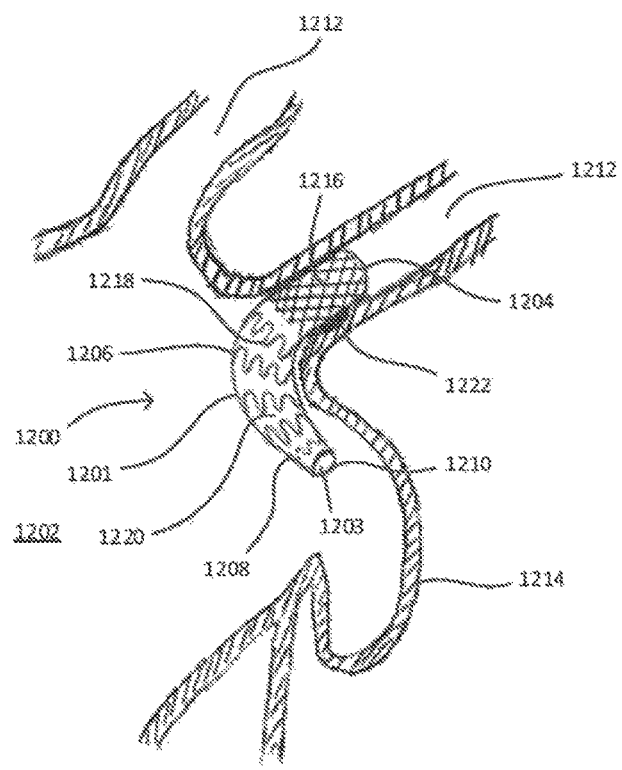
FIG. 13 is a partial cross-sectional view of a left atrium of a human heart showing another embodiment of a conduit anchored in a pulmonary vein and including an outlet portion having a tapered shape.

Referring to FIG. 13, there is shown another embodiment of a conduit 1200 in a partial cross-section of a left atrium 1202 of a human heart. The conduit 1200 can comprise a generally tubular body or sleeve 1201 defining a lumen 1203 and including an inlet portion 1204, an elbow portion 1206, and an outlet portion 1208. The inlet portion 1204 can comprise an inlet stent or frame 1216 for anchoring the inlet portion 1204 in a pulmonary vein 1212, as described above. The elbow portion 1206 and the outlet portion 1208 can comprise one or more annular hoops 1218 and a covering or sleeve 1220 extending over the inlet frame 1216 and the hoops 1218. The outlet portion 1208 can comprise a substantially tapered shape such that the diameter of the outlet 1210 is smaller than the diameter of the elbow portion 1206. In this manner, blood can be directed from the pulmonary vein 1212 into the LAA 1214 at a higher velocity than that at which the blood otherwise enters the LAA 1214. The conduit 1200 can also comprise a radiopaque or otherwise discernible marker 1222 for purposes of assessing the rotational orientation of the conduit 1200 during implantation of the conduit to ensure that the outlet 1210 is pointed substantially toward the LAA 1214. It should be understood that a marker such as the marker 1222 can be used in combination with any of the embodiments disclosed herein.

Figure 14:
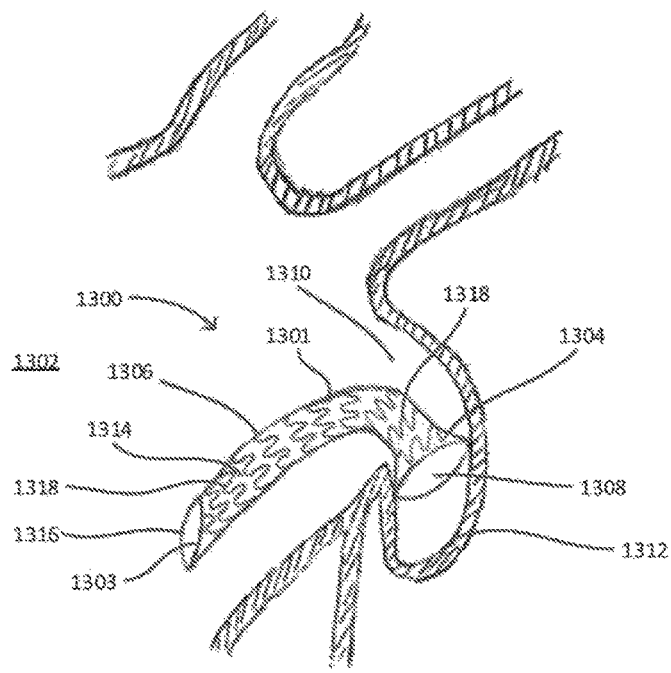
FIG. 14 is a partial cross-sectional view of a left atrium of a human heart showing another embodiment of a conduit including an inlet portion configured to be anchored in the LAA.

Referring to FIG. 14, there is shown another embodiment of a conduit 1300 in a partial cross-section of a left atrium 1302 of a human heart. The conduit 1300 comprises a generally tubular body or sleeve 1301 defining a lumen 1303 and including an inlet portion 1304 having one or more annular hoops 1318. The conduit 1300 can also have an outlet portion 1306 including an outlet 1316 and one or more annular hoops 1318. A covering 1314 can extend over the annular hoops 1318 along the entire length of the conduit 1300. The inlet portion 1304 can comprise a flared inlet 1308 generally in the shape of the bell of a trumpet. In the embodiment shown, the inlet portion 1304 does not occlude the entire ostium 1310 of the LAA 1312, but rather contacts the walls of the LAA 1312 at points about 180° apart in a manner similar to the conduit of FIG. 1C. In this manner, the inlet portion 1304 acts to restrain the conduit 1300 in the LAA 1312. The outlet 1316 can be oriented substantially in the direction of the mitral valve (not shown) and can induce a pressure differential between the inlet portion 1304 and the outlet 1316 by way of a Bernoulli-type action in a manner similar to the conduit of FIG. 2. In this manner, blood is induced to flow out of the LAA 1312 through the conduit 1300.

Figure 15:
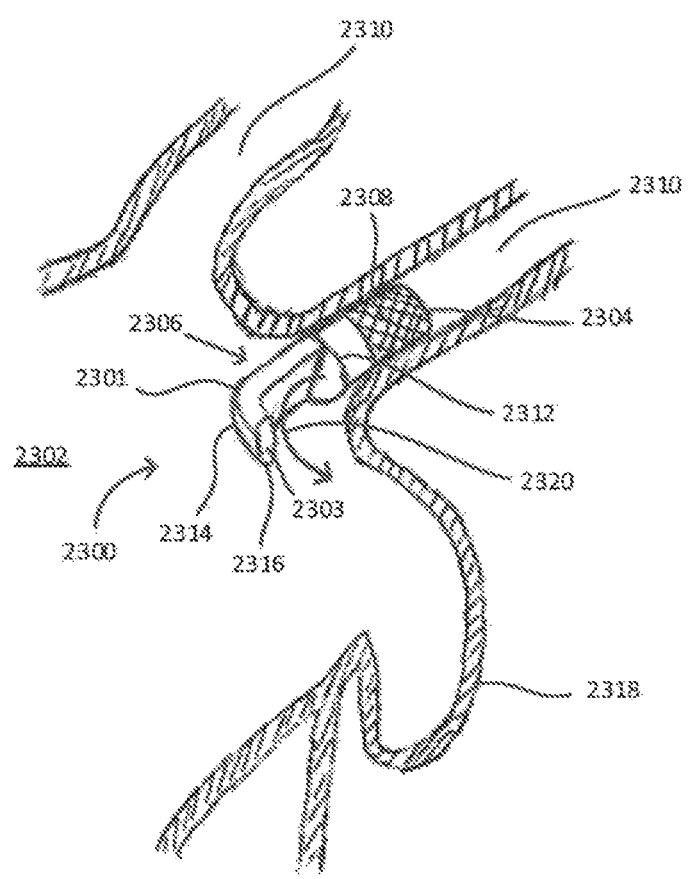
FIG. 15 is a partial cross-sectional view of a left atrium of a human heart showing another embodiment of a conduit anchored in a pulmonary vein and including an outlet portion comprising a tubular portion and an elbow portion.

Referring to FIG. 15, there is shown another embodiment of a conduit 2300 in a partial cross-section of a left atrium 2302 of a human heart. The conduit 2300 can comprise a tubular main body 2301 defining a lumen 2303 and including an inlet portion 2304 and an outlet portion generally indicated at 2306. The inlet portion 2304 can comprise an inlet stent or frame 2308 for anchoring the inlet portion 2304 in a pulmonary vein 2310, as described above. The outlet portion 2306 can comprise a tubular portion 2312 and an elbow portion 2314 having a terminal end 2316 that can be oriented substantially in the direction of the LAA 2318. The elbow portion 2314 can comprise a substantially curved shape, and can be configured to direct a flow of blood from the pulmonary vein 2310 toward the LAA 2318 in the manner shown by flow line 2320.

Figure 31:
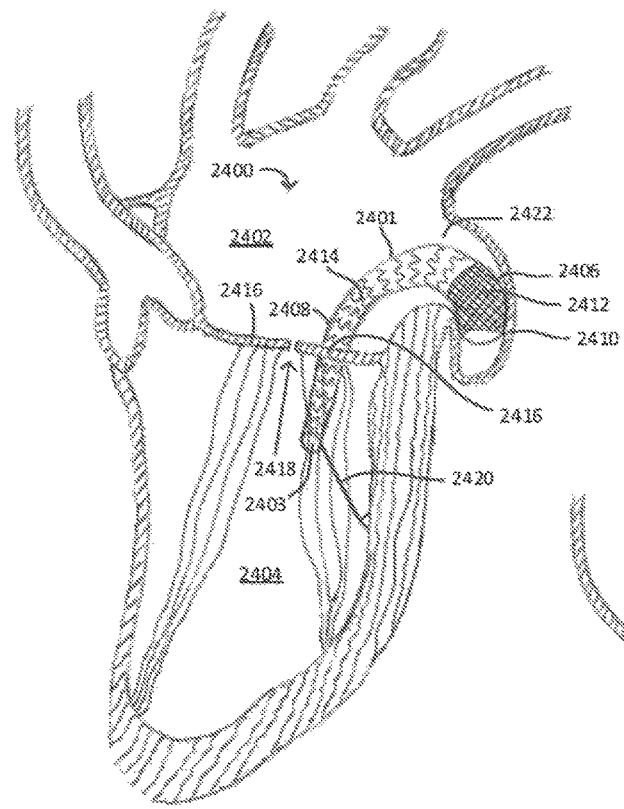
FIG. 31 is a cross-sectional view of a left atrium and a left ventricle of a human heart showing another embodiment of a conduit anchored in the LAA and extending through the mitral valve.

Referring to FIG. 31, there is shown another embodiment of a conduit 2400 in a cross-sectional view of a left atrium 2402 and a left ventricle 2404 of a human heart. The conduit 2400 comprises a generally tubular body or sleeve 2401 defining a lumen 2403 and including an inlet portion 2406 and an outlet portion 2408. The inlet portion 2406 can include an expandable stent or frame 2412, and the outlet portion can include one or more annular hoops 2414, similar to the conduits of FIGS. 2 and 14. The inlet portion 2406 is configured to be placed into a LAA 2410. The outlet portion 2408 is configured to extend into the left ventricle 2404 through the leaflets 2416 of the mitral valve 2418, where the pressure differential between the left atrium 2402 and the left ventricle 2404 can induce a Bernoulli-type effect similar to the conduits of FIGS. 2 and 14. In this manner, blood can be induced to flow into and/or out of the LAA 2410 through the lumen 2403 of the conduit 2400.

The outlet portion 2408 can extend through a surgical opening in one of the native mitral valve leaflets 2416, and therefore is held in place within the left ventricle 2404. In other embodiments, the outlet portion 2408 can extend between the two native leaflets 2416 and can be held in place within the left ventricle 2404 by an optional anchoring device 2420, one end of which can be anchored to tissue within the left ventricle 2404. Alternatively, the anchoring device 2420 can be configured to clamp or clip onto the papillary muscles or one of the two native leaflets 2416. In alternative embodiments, the inlet portion 2406 can comprise a flared inlet similar to the conduit of FIG. 14. Also, the inlet portion 2406 can occupy substantially the entire ostium 2422 of the LAA 2410, or can contact the walls of the LAA at points about 180° apart in a manner similar to the conduit of FIG. 1C.

Figure 32:
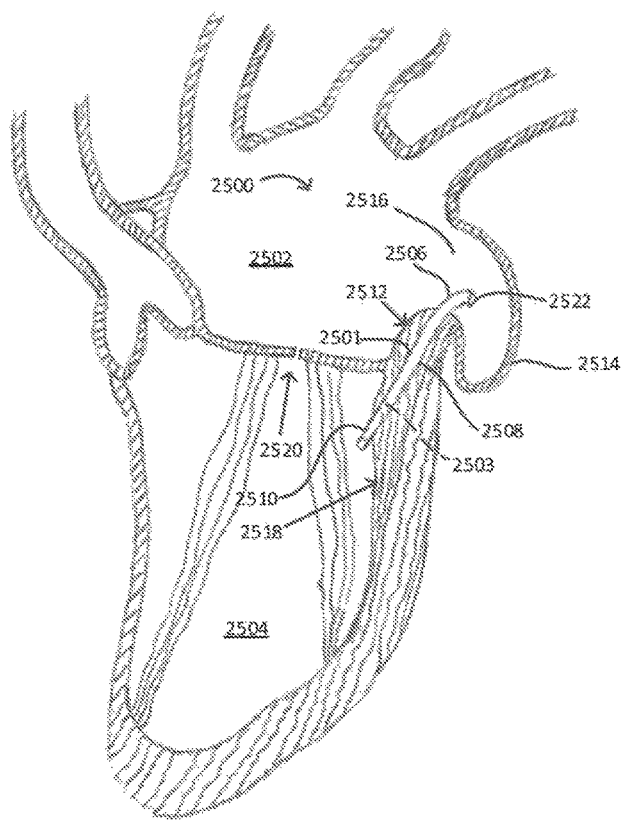
FIG. 32 is a cross-sectional view of a left atrium and a left ventricle of a human heart showing another embodiment of a conduit embedded in the left atrial and left ventricular walls.

Referring to FIG. 32, there is shown another embodiment of a conduit 2500 in a cross-sectional view of a left atrium 2502 and a left ventricle 2504 of a human heart. The conduit 2500 comprises a generally tubular body 2501 defining a lumen 2503 (indicated in phantom) and including an inlet portion 2506, an intermediate portion 2508, and an outlet portion 2510. The conduit 2500 can be disposed through the tissue of the left atrial wall 2512 and the left ventricular wall 2518 such that the intermediate portion 2508 of the conduit 2500 is embedded in, and held in place by, the walls 2512, 2518. The inlet portion 2506 can emerge from the left atrial wall 2512 substantially at or near the ostium 2516 of the LAA 2514, and can be curved such that an inlet 2522 is oriented substantially toward or within the LAA 2514. Similarly, the outlet portion 2510 can emerge from the left ventricular wall 2518 below the mitral valve 2520. In this manner, the outlet portion 2510 can be located substantially within, or in communication with, the left ventricle 2504.

The pressure differential between the left atrium 2502 and the left ventricle 2504 can induce blood to flow into and/or out of the LAA 2514 and into the left ventricle 2504 through the lumen 2503 of the conduit 2500, similar to the conduits of FIGS. 2, 14, and 31. In alternative embodiments, the conduit can comprise hooks or barbs (not shown) to engage the tissue of the walls 2512, 2518 to hold the conduit in place. The conduit 2500 depicted in FIG. 32 does not include any metal supports (e.g., stents or rings) but can include such supports to increase the strength of the conduit 2500 and/or to ensure that the sleeve 2501 remains in an open configuration through its length once implanted. The conduit 2500 can be implanted by forming an opening in the walls 2512, 2518, and then inserting the conduit 2500 into the opening. In alternative embodiments, the conduit 2500 is configured to be pushed through the tissue of walls 2512, 2518 for implanting the conduit 2500.

Figure 33:
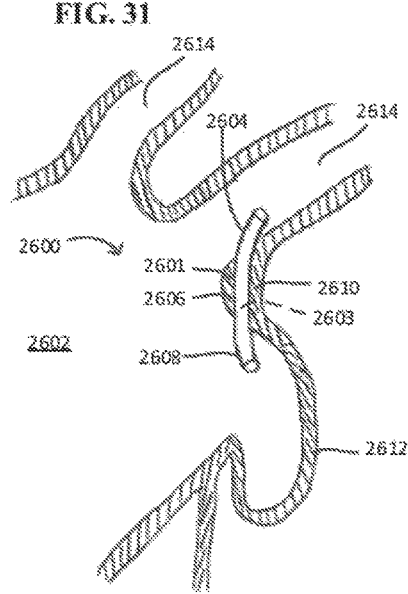
FIG. 33 is a partial cross-sectional view of a left atrium of a human heart showing another embodiment of a conduit embedded in the tissue between a pulmonary vein and the LAA.

Referring to FIG. 33, there is shown another embodiment of a conduit 2600 in a partial cross-section of a left atrium 2602 of a human heart. The conduit 2600 comprises a generally tubular body 2601 defining a lumen 2603 (indicated in phantom) and including an inlet portion 2604, an intermediate portion 2606, and an outlet portion 2608. The conduit 2600 can be disposed through the tissue 2610 between the LAA 2612 and a pulmonary vein 2614 such that the intermediate portion 2606 is retained by the tissue 2610. The inlet portion 2604 can be located substantially within the pulmonary vein 2614, and the outlet portion 2608 can be located substantially within the LAA 2612. In this manner, the conduit 2600 can direct a flow of blood through the lumen 2603 from the pulmonary vein 2614 into the LAA 2612. In alternative embodiments, the intermediate portion 2606 can comprise hooks or barbs (not shown) so as to engage the tissue 2610 to hold the conduit 2600 in place. Although the conduit 2600 depicted in FIG. 33 does not include any metal supports (e.g., stents or rings), the conduit 2600 can include such supports for increased strength or to maintain an open configuration. The conduit can be implanted by pushing the conduit through tissue 2610 or by forming an opening in tissue 2610 and inserting the conduit 2600 in the opening.

Turning now to methods of implantation, a conduit, including any of the embodiments described in this application, may generally be loaded into a delivery sheath of an elongated delivery catheter and advanced percutaneously through a patient's vasculature into the heart of a patient without placing the patient on a cardiopulmonary bypass pump (e.g., "off pump"). Generally, a hollow delivery catheter may be inserted into a blood vessel of a patient and advanced through the vessel toward the heart. For example, a conduit can be delivered in an antegrade approach in which the delivery catheter is inserted into a vein (e.g., a femoral vein) and advanced into the right atrium. Once inside the right atrium, the catheter may pierce the interatrial septum to gain access to the left atrium. From there, the conduit can be positioned in a pulmonary vein and/or the LAA as desired and deployed by advancing the conduit from the distal end of the sheath. Alternatively, the delivery catheter can enter the heart through the left ventricle and can be advanced transapically into the left atrium through the mitral valve, where the conduit may be located in a pulmonary vein and/or the LAA as desired. In another procedure, the delivery catheter can be advanced in a retrograde approach through a femoral artery, through the aorta into the left ventricle, and then through the mitral valve to gain access to the left atrium. The conduit may also be implanted by an open surgical method in which the heart is exposed directly. In cases where a conduit is implanted in an open heart procedure, the conduit need not be radially compressible or collapsible to a radially collapsed or crimped configuration for delivery into the body. Alternatively, the conduit may be implanted through a closed-heart, open-chest surgical procedure (e.g., an "off-pump" procedure), or a minimally invasive procedure where the conduit can be introduced through a small opening in the chest such as, for example, through an intercostal space.

Figure 16A:
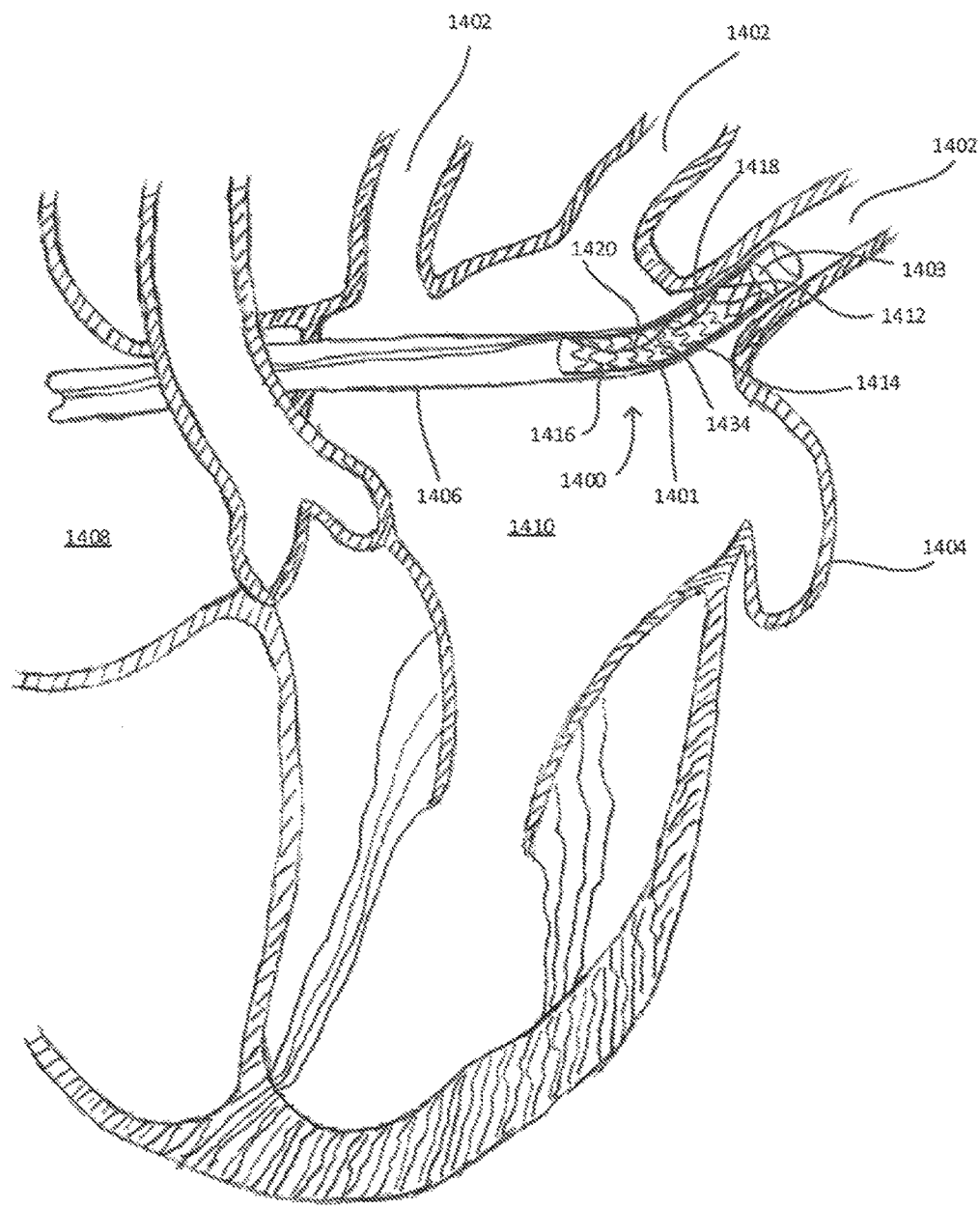
FIG. 16A is a cross-sectional view of a human heart showing an exemplary embodiment of a delivery sheath containing a conduit entering a left atrium via an inter-atrial septum.

FIGS. 16A-16F depict a method of implanting a conduit 1400 in a pulmonary vein 1402 to increase blood flow volume and velocity in a LAA 1404. FIG. 16A depicts a delivery sheath 1406 of a delivery apparatus containing the conduit 1400 advanced into a pulmonary vein 1402 prior to deployment of the conduit 1400. The delivery sheath 1406 can access the right atrium 1408, shown in partial cross-section in FIG. 16A, percutaneously from outside a patient's body in the manner described above. The delivery sheath 1406 can then be advanced transseptally into the left atrium 1410 and into a pulmonary vein 1402, as shown in FIG. 16A.

Figure 16B:
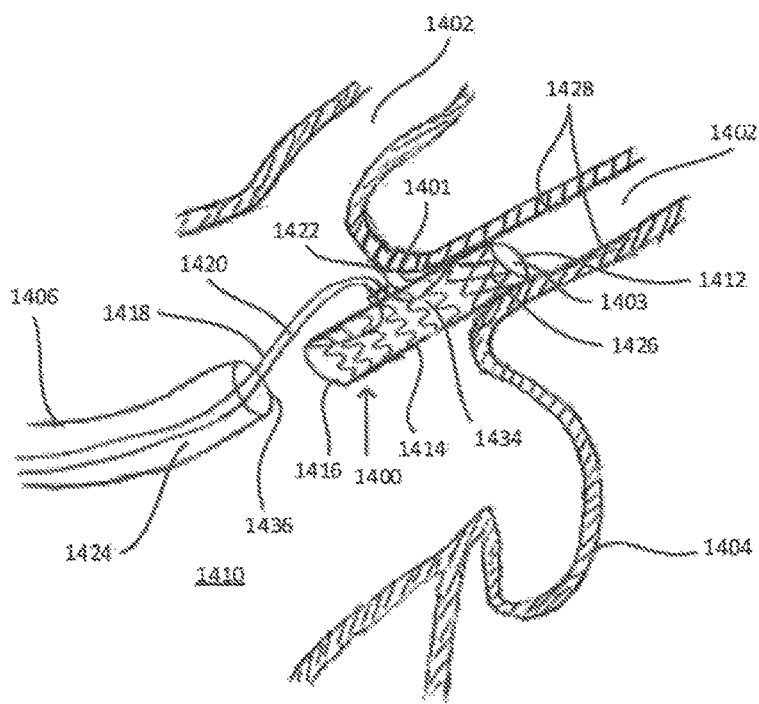
FIG. 16B is a partial cross-sectional view of the human heart of FIG. 16A showing the placement of the conduit in a pulmonary vein.

The conduit 1400 can comprise a generally tubular body or sleeve 1401 defining a lumen 1403 and including an inlet portion 1412, an intermediate portion 1414, and an outlet portion 1416. The inlet portion 1412 can comprise an inlet frame or stent 1426 for anchoring the inlet portion 1412 in the pulmonary vein 1402. The intermediate portion 1414 and outlet portion 1416 can also comprise one or more annular hoops covered by a sleeve or covering 1434. The intermediate portion 1414 can comprise a substantially flexible zone which can either be pre-formed into a curved shape in the manner of the conduit of FIG. 1, or which can be folded or bent into a curved shape by manipulating first and second guide wires 1418, 1420, respectively, once the inlet portion 1412 is placed into the pulmonary vein 1402. The guide wires 1418, 1420 can be affixed to the interior wall of the conduit 1400, and can emerge from the conduit through an access port 1422, as best shown in FIG. 16B. The guide wires 1418, 1420 can be threaded through the lumen 1424 of the delivery sheath 1406 to a handle portion at the proximal end of the delivery apparatus, and can thereby be manipulated from outside the body. Also, as discussed with respect to the preceding embodiments, the conduit 1400 may be crimped into a radially compressed or collapsed state and loaded into the delivery sheath 1406 for delivery into the body of a patient as shown.

FIG. 16B shows the conduit 1400 of FIG. 16A implanted in the pulmonary vein 1402 with the delivery sheath 1406 partially withdrawn. After the delivery sheath 1406 is advanced into the pulmonary vein 1402 a sufficient distance to position the inlet frame 1426 within the pulmonary vein 1402, the conduit 1400 is advanced from the delivery sheath 1406 by pushing the conduit 1400 out of the delivery sheath 1406 or retracting the sheath relative to the conduit. A pusher member extending axially through the delivery sheath 1406 can be provided to assist in deploying the conduit 1400 from the sheath. The inlet frame 1426 can then expand to contact the walls of the pulmonary vein 1402 to anchor the conduit 1400 in place. The first and second guide wires 1418, 1420, are shown emerging from the access port 1422 and trailing back through the lumen 1424 of the delivery sheath 1406.

Figure 16C:
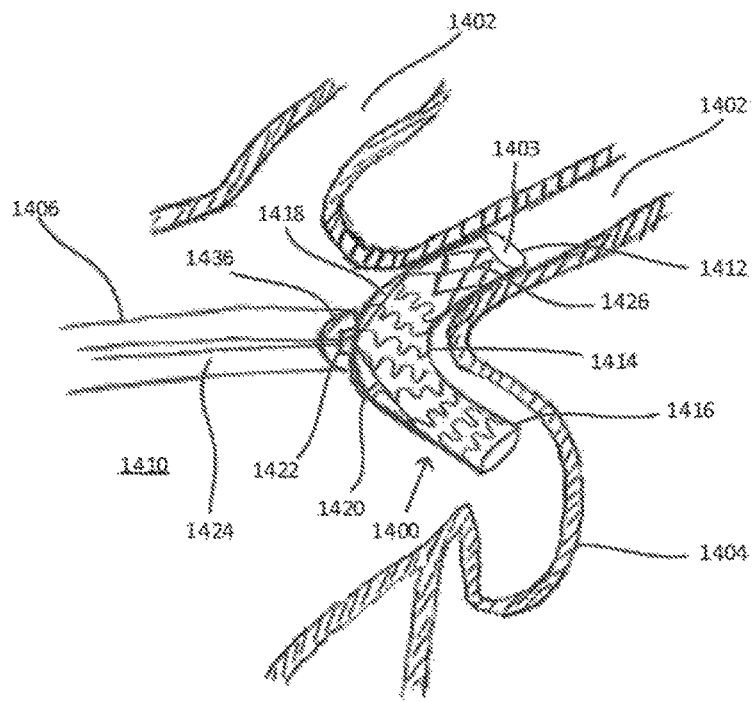
FIG. 16C is a partial cross-sectional view of the human heart of FIG. 16A showing the bending of the conduit into a curved shape using guide wires.

After the inlet portion 1412 is placed in the pulmonary vein 1402 the conduit 1400 may be bent into a curved shape as shown in FIG. 16C. The conduit can be bent into a curved shape by tensioning the first and second guide wires 1418, 1420 by forces applied to the guide wires 1418, 1420 from outside the patient's body. The end of the first wire 1418 is secured inside the conduit 1400 within the inlet portion 1412, while the end of the second wire 1420 is secured inside the conduit 1400 within the outlet portion 1416. This causes the conduit 1400 to bend when tension is applied to the wires. While placing the opening 1436 of the delivery sheath 1406 adjacent the access port 1422, tension can be evenly applied to both guide wires 1418, 1420 to cause the conduit 1400 to bend into the desired shape as shown in FIG. 16C. The opening 1436 of the delivery sheath 1406 may even be placed in contact with middle portion 1414 of the conduit substantially over the access port 1422 to allow the delivery sheath 1406 to be used as a support for the conduit 1400 as it is bent into the final shape. Alternatively, the guide wires 1418, 1420 can be secured to the outside of the inlet and outlet portions 1412, 1416 of the conduit 1400.

Figure 16D:
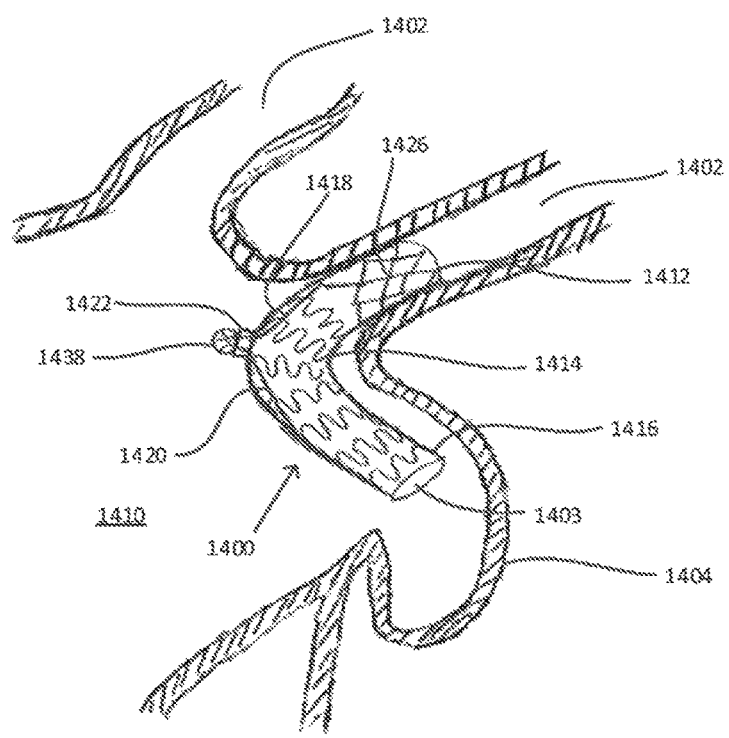
FIG. 16D is a partial cross-sectional view of the human heart of FIG. 16A showing the final placement of the conduit with the guide wires tied together.

FIG. 16D shows a first alternative embodiment of the conduit 1400 in its final position in which the first and second guide wires 1418, 1420 are cut or severed outside the port and the remaining ends are tied together in a knot 1438 or are otherwise secured at or near the access port in a manner so as to remain in a tensioned state. By leaving the guide wires 1418, 1420 in a tensioned state, the conduit 1400 retains its desired shape after implantation.

Figure 16E:
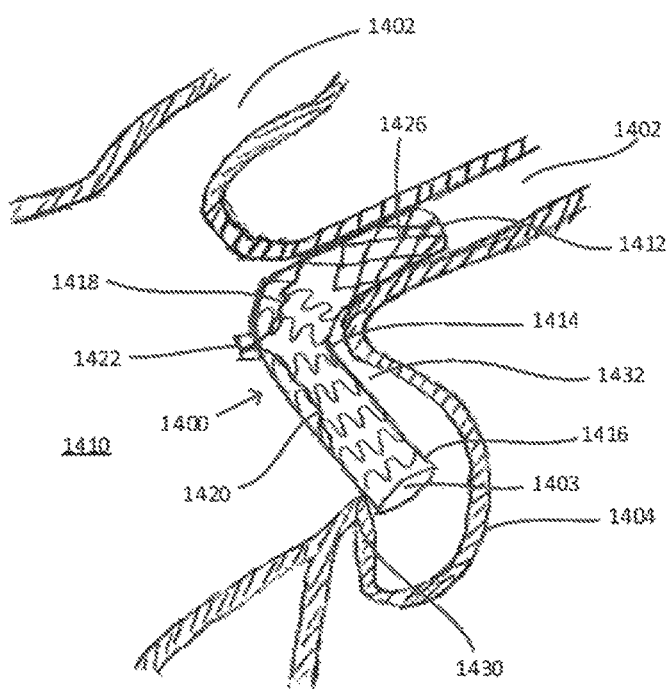
FIG. 16E is a partial cross-sectional view of the human heart of FIG. 16A showing the final placement of the conduit with an outlet portion resting against an ostium of a LAA and the guide wires cut.

Alternatively, FIG. 16E shows the final positioning of an alternative embodiment of the conduit 1400 in which the guide wires 1418, 1420 are cut and remain inside the conduit 1400 after implantation. As shown in FIG. 16E, the outlet portion 1416 can also rest against the tissue 1430 of the interior of the LAA 1404 surrounding the ostium 1432. In this manner, the outlet portion 1416 of the conduit 1400 remains stabilized in the LAA 1404 and the curved shape of the intermediate portion 1414 can be maintained without tension in the guide wires and regardless of whether the curvature was pre-formed.

Figure 16F:
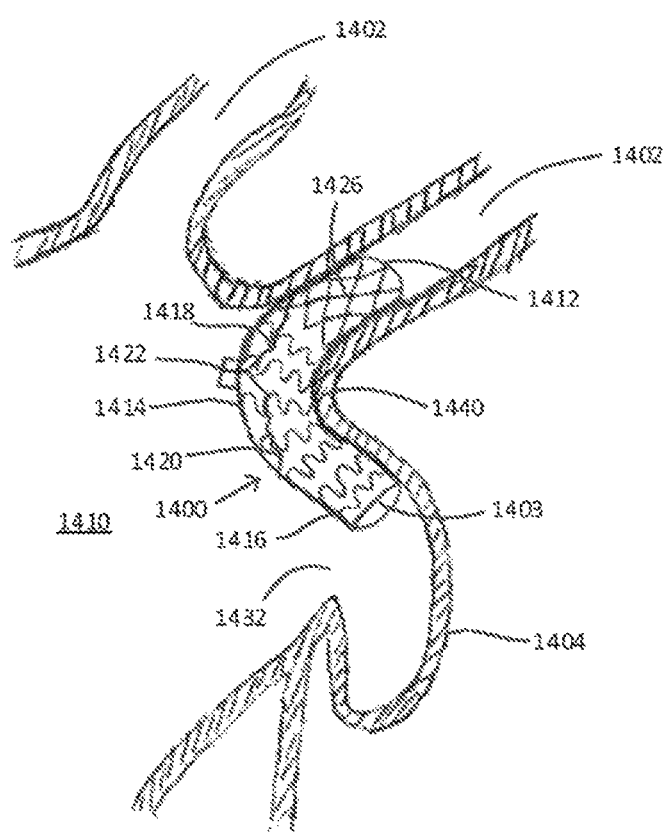
FIG. 16F is a partial cross-sectional view of the human heart of FIG. 16A showing the conduit clamping tissue between the pulmonary vein and the LAA.

Alternatively, the conduit 1400 can be configured such that it clamps or pinches the tissue 1440 between the LAA and the pulmonary vein 1402, as shown in FIG. 16F. The clamping action can be achieved with or without use of the guide wires (e.g., the clamping action can be achieved by manipulating the guide wires, or by, for example, configuring the implant such that it is biased to curve inward and clamp the tissue 1440).

Figure 17A:
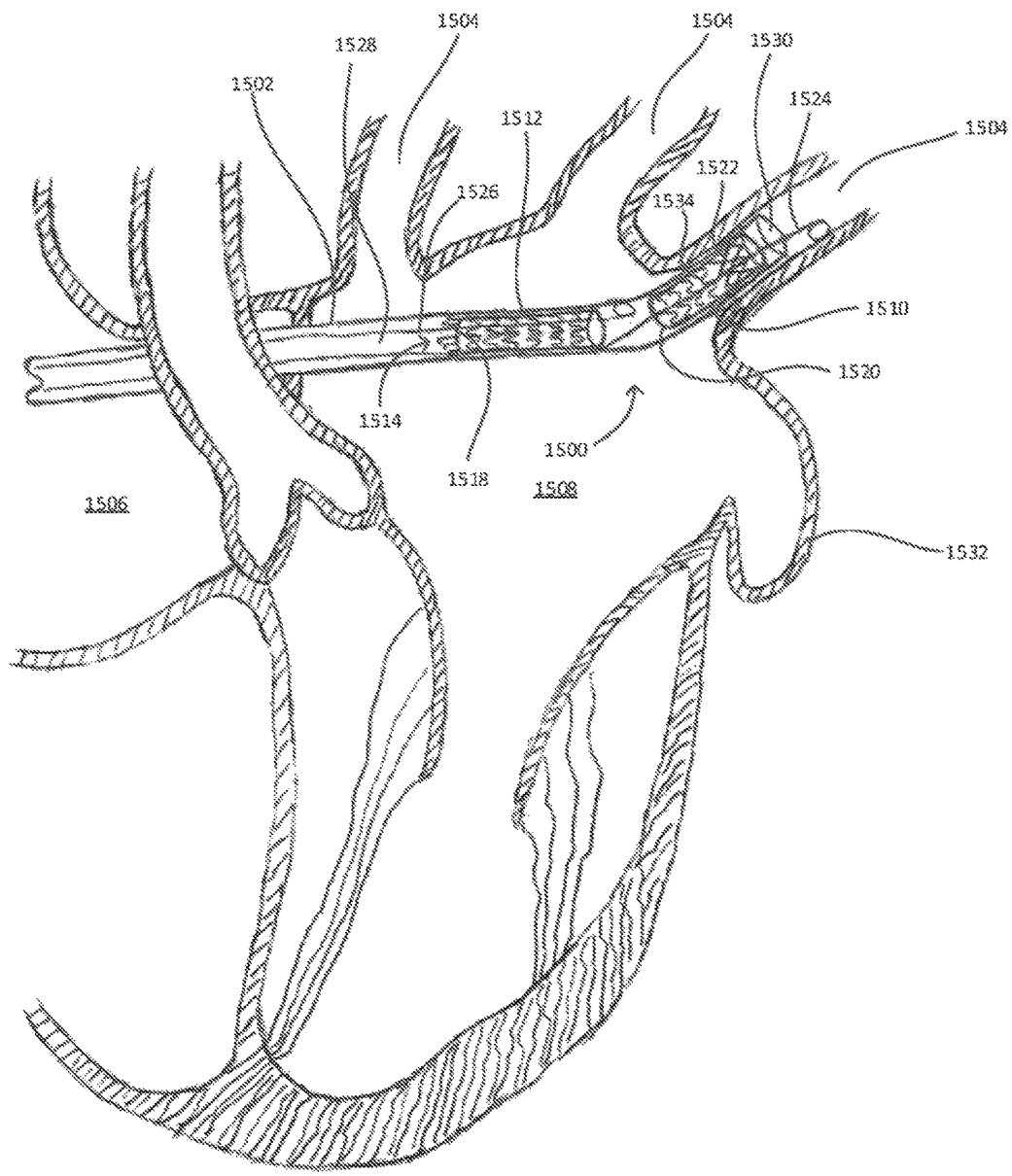
FIG. 17A is a partial cross-sectional view of a human heart showing a delivery sheath containing two separate portions of a conduit entering a left atrium via an inter-atrial septum.
Figure 17B:
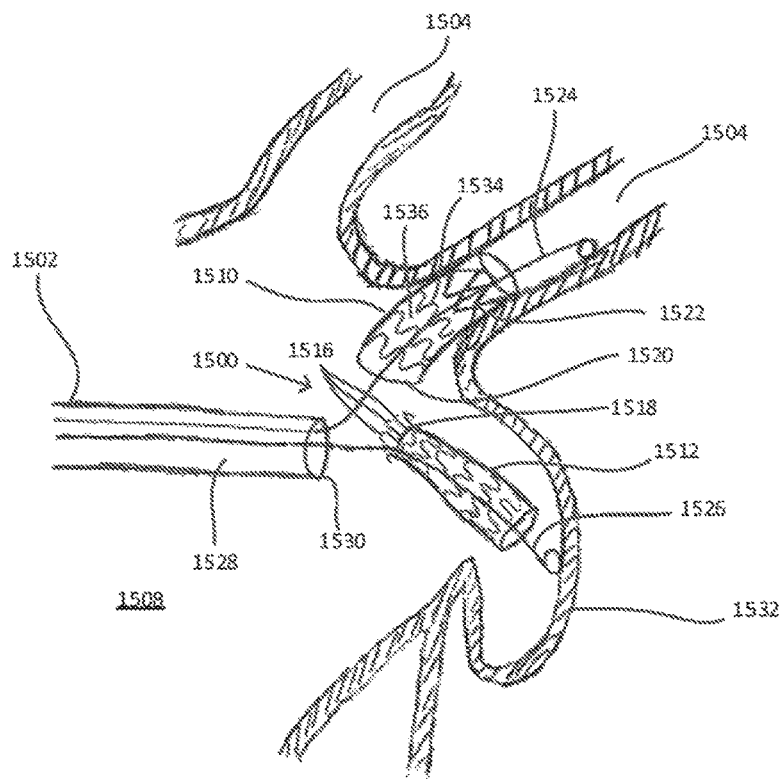
FIG. 17B is a partial cross-sectional view of the human heart of FIG. 17A showing the placement of the first half of the conduit in a pulmonary vein and the second half in a LAA.
Figure 17C:
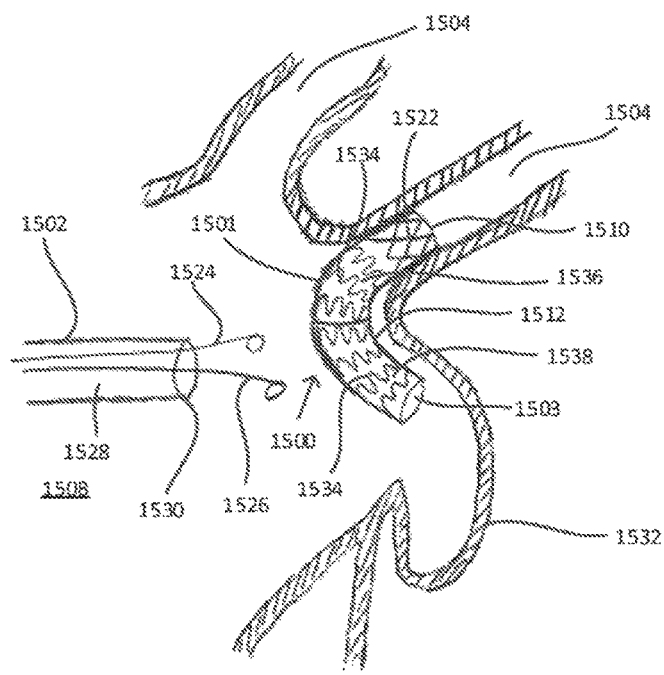
FIG. 17C is a partial cross-sectional view of the human heart of FIG. 17A showing the final placement and attachment of the two halves of the conduit.

FIGS. 17A-17C depict a method of implanting another embodiment of a conduit 1500 comprising providing a delivery sheath 1502 containing the conduit 1500 and advancing the delivery sheath 1502 into a pulmonary vein 1504 prior to deployment of the conduit 1500, as shown in FIG. 17A. The delivery sheath 1502 can access the right atrium 1506, shown in partial cross-section in FIG. 17A, percutaneously from outside a patient's body in the manner described above. The delivery sheath 1502 can then be advanced transseptally into the left atrium 1508 and into a pulmonary vein 1504.

The conduit 1500 can comprise a generally tubular body or sleeve 1501 (FIG. 17C) defining a lumen 1503 and including an inlet portion and an outlet portion 1510, 1512. In the embodiment shown, the inlet and outlet portions 1510, 1512 are separate components that are loaded into the delivery sheath 1502 and joined together once inside the left atrium 1508. The inlet portion 1510 can comprise an inlet stent or frame 1522 for anchoring the inlet portion 1510 in the pulmonary vein 1504, as described above, and one or more annular hoops 1534, which can be covered by a sleeve or covering 1536, as shown in FIG. 17B. The outlet portion 1512 can comprise a mechanism generally indicated at 1514 for securing the inlet and outlet portions 1510, 1512 together. In the embodiment shown, the mechanism 1514 can comprise a plurality of hooks 1516 disposed circumferentially around the inlet 1518 of the outlet portion 1512. The plurality of hooks 1516 can be configured to be placed inside the outlet 1520 of the inlet portion 1510 and engage the interior of the inlet portion 1510 (for example, the inlet frame 1522 of the inlet portion 1510), as best shown in FIGS. 17B-17C. In some embodiments, a band or a suture can be placed around the outlet portion 1512 near the inlet 1518 so that the diameter of the inlet 1518 when deployed from the sheath is smaller than the diameter of outlet 1520 of the inlet portion 1510, allowing for insertion of the outlet portion 1512 into the inlet portion 1510. The outlet portion 1512 can also comprise one or more annular hoops 1534, which can be covered by a sleeve or covering 1538.

Conduit 1500 can be manipulated into place with the aid of first and second guide wires 1524, 1526, which can be threaded through a lumen 1528 of the delivery sheath 1502, as shown in FIG. 17A. More specifically, the first guide wire 1524 is threaded through the inlet portion 1510 but extends along the outside of the outlet portion 1512 as it extends through the lumen 1528, and the second guide wire 1526 is threaded through the outlet portion 1512 but does not advance forward through the inlet portion 1510, as shown in FIGS. 17A-17B. In this manner, the inlet and outlet portions may each be manipulated into different locations without interfering with the other.

Inlet and outlet portions 1510, 1512, respectively, can be loaded sequentially into delivery sheath 1502 with the inlet portion 1510 nearest the outlet 1530 of the delivery sheath so as to facilitate location of the inlet portion in the pulmonary vein 1504 first. The delivery sheath 1502 is first advanced inside pulmonary vein 1504, and first guide wire 1524 is then advanced out of the delivery sheath inside the pulmonary vein to aid with advancement of the inlet portion 1510, as shown in FIG. 17A. Once the delivery sheath 1502 is advanced into the pulmonary vein 1504 a sufficient distance to position the inlet frame 1522 of the inlet portion within the pulmonary vein, the inlet portion 1510 may be advanced from the delivery sheath into the vein. Upon advancing from the lumen 1528 of the delivery sheath, the inlet frame 1522 can expand to contact the walls of the pulmonary vein 1504 to anchor the inlet portion 1510 in place. In this manner, the inlet portion 1510 can be fully advanced into the pulmonary vein and the delivery sheath 1502 can be withdrawn back into the left atrium 1508.

Once the inlet portion 1510 is located in the pulmonary vein 1504, the delivery sheath 1502 may be realigned for positioning of the outlet portion 1512, as shown in FIG. 17B. The second guide wire 1526 is first advanced into the LAA 1532 and, with the first guide wire 1524 still in place in the pulmonary vein 1504, the outlet portion 1512 can be advanced from the delivery sheath into the LAA 1532. Next, the inlet 1518 of the outlet portion 1512 can be advanced into the outlet 1520 of the inlet portion 1510 by manipulation of the first and second guide wires 1524, 1526. Once inside the inlet portion, the outlet portion 1512 can be expanded, such as by removing a band placed around the outlet portion, to allow the plurality of hooks 1516 to engage the inlet portion 1510, thereby fastening the inlet and outlet portions together to form the completed conduit 1500, as shown in FIG. 17C. Other techniques or mechanisms can be used to connect the ends of the inlet and outlet portions 1510, 1512. For example, in some embodiments the adjacent ends of the inlet and outlet portions 1510, 1512 can have magnets that pull together and connect the adjacent panels or end portions.

Figure 18:
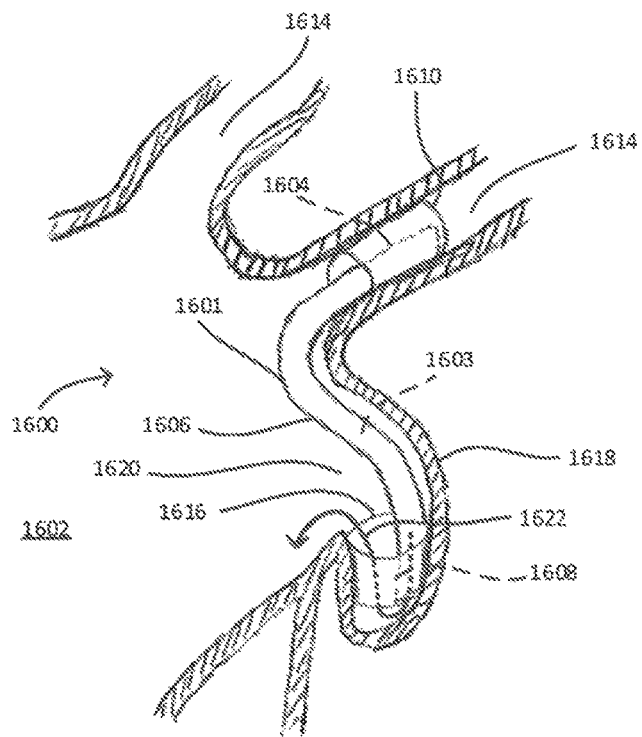
FIG. 18 is a partial cross-sectional view of a left atrium of a human heart showing another embodiment of a conduit configured to partially divert a flow of blood from a pulmonary vein.

FIG. 18 depicts another embodiment of a conduit 1600 in a partial cross-section of a left atrium 1602 of a human heart. The conduit 1600 can comprise a generally tubular body or sleeve 1601 defining a lumen 1603 and including an inlet portion 1604, an intermediate portion 1606, and an outlet portion 1608. The inlet portion 1604 can be affixed inside a first stent or frame 1610, which can be located in a pulmonary vein 1614 and configured to anchor the conduit 1600 in that vein. The outlet portion can be affixed inside a second stent or frame 1616, which can be located in a LAA 1618, and configured to anchor the outlet portion 1608 in the LAA 1618. The first and second frames 1610, 1616 can have substantially the same characteristics and construction as described with respect to the frames discussed above. As can be seen from FIG. 18, first and second frames 1610, 1616 can be configured such that their respective diameters are greater than the diameter of the sleeve 1601. In this manner, blood flowing from the pulmonary vein 1614 can be partially diverted into the sleeve 1601, and thereby directed into the LAA 1618. The larger diameter of the second frame 1616 can allow blood flowing from the outlet portion into the LAA to flow out of the LAA through the second frame 1616 and the ostium 1620 as indicated by flow line 1622. The sleeve 1601 as depicted in FIG. 18 does not include any metal supports (e.g., stents or rings) but can include such supports to increase the strength of the sleeve 1601 and/or to ensure the sleeve remains in an open configuration throughout its length once implanted.

Figure 19:
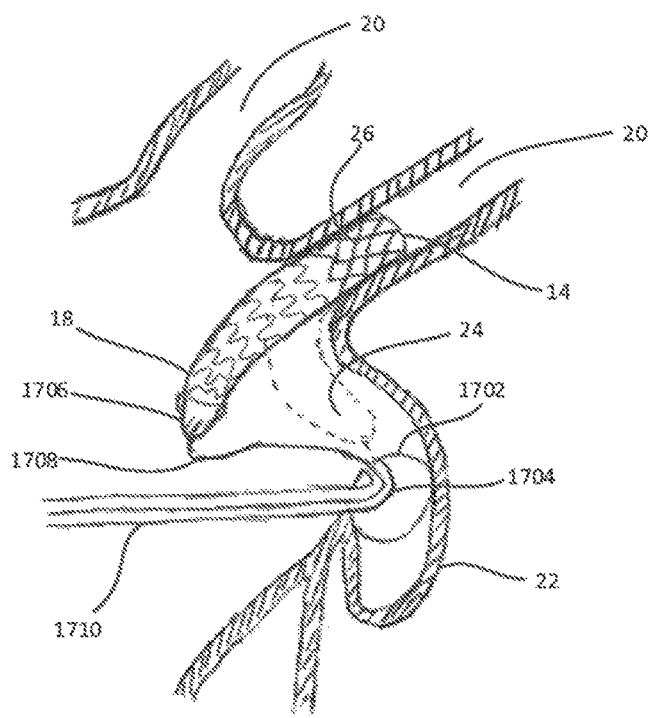
FIG. 19 is a partial cross-sectional view of a left atrium of a human heart showing another exemplary method of implanting a conduit with an anchor and a detachable nose cone.

FIG. 19 depicts a method of implanting the conduit of FIG. 1 comprising providing a pulley mechanism 1702 having an internal lumen 1704, and locating the pulley mechanism 1702 in the ostium 24 of the LAA 22. The pulley mechanism 1702 can be an inflatable balloon or equivalent mechanism. The inlet portion 14 of the conduit can be positioned in the pulmonary vein 20 and the inlet frame 26 can be radially expanded to anchor the conduit in the pulmonary vein 20, as described above. The outlet frame 32 (see FIG. 1) of the outlet portion 18 can be retained in a radially compressed or collapsed state inside a detachable nose cone 1706. The detachable nose cone 1706 can be tethered to a guide wire 1708 which can be threaded through the lumen 1704 of the pulley mechanism 1702 and out of the body through a catheter or sheath 1710. The outlet portion 18 can be maneuvered into the LAA 22 by pulling on the guide wire 1708, as shown in phantom in FIG. 19. Once in place, the nose cone 1706 can be detached from the outlet portion and the outlet frame 32 can be allowed to expand to anchor the outlet portion 18 in the LAA 22. In addition to the nose cone 1706, the outlet frame 32 can be contained in a radially compressed or collapsed state by sutures (not shown), which can be cut or released when the nose cone 1706 is removed.

FIGS. 20A-20D depict a method of implanting a conduit 1800 comprising providing a delivery sheath or catheter 1802 containing a conduit 1800, a plunger or pusher member 1804, and first and second guide wires 1806, 1808, respectively. The delivery sheath 1802 can access the left atrium 1810 transseptally in the manner described above. The conduit 1800 can comprise a generally tubular body or sleeve 1801 defining a lumen 1803 (see, e.g., FIGS. 20C and 20D), and can include an inlet portion 1812, an intermediate portion 1814, and an outlet portion 1816. The inlet, intermediate, and outlet portions can be portions of a single frame or stent 1818, which can have the same properties and construction as the frames discussed above. For example, the inlet portion 1812 of the frame 1818 can expand to anchor the conduit in the pulmonary vein 1828, and the outlet portion 1816 of the frame 1818 can expand to anchor the conduit 1800 in the LAA 1820. The frame 1818 can also be covered with a flexible sleeve, or cover, 1822.

Figure 20A:
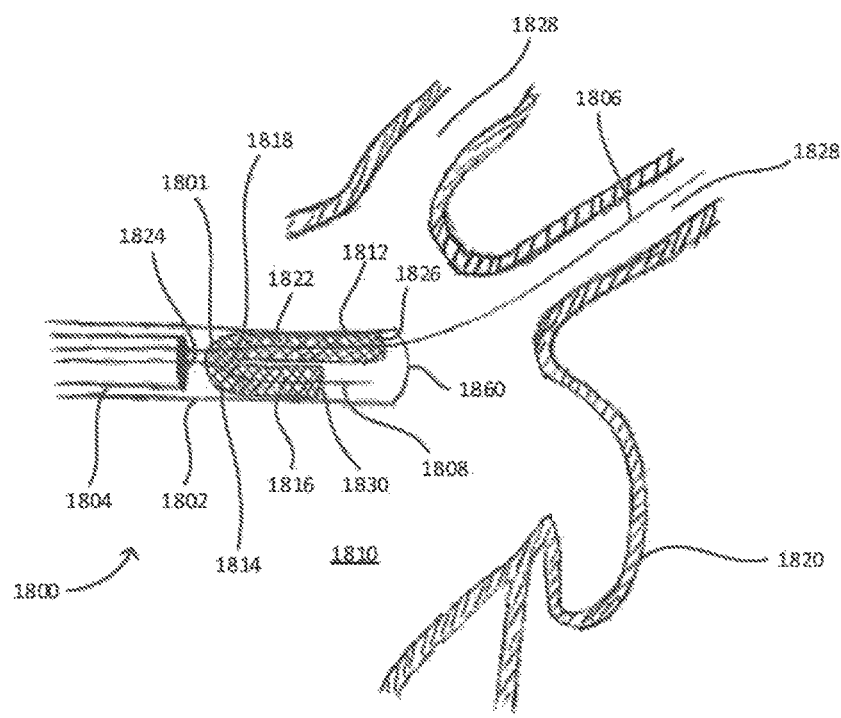
FIG. 20A is a partial cross-sectional view of a left atrium of a human heart showing a delivery sheath containing a folded conduit, according to another embodiment.

The conduit 1800 can be folded on itself and loaded into the delivery sheath 1802 in a radially compressed or collapsed state such that the inlet portion 1812 extends beyond the outlet portion 1816 (e.g., the inlet and outlet portions 1812, 1816 are staggered such that the inlet portion is closer to the outlet 1860 of the delivery sheath 1802), as shown in FIG. 20A. The first guide wire 1806 can extend through the distal opening 1824 of the plunger 1804, through the intermediate portion 1814, and out of the inlet 1826 of the inlet portion 1812. The first guide wire 1806 can then be advanced into the pulmonary vein 1828 in preparation for unsheathing the conduit 1800. Similarly, the second guide wire 1808 can extend through the opening 1824 of the plunger 1804, through the intermediate portion 1814, and out of the outlet 1830 of the outlet portion, as shown in FIG. 20A.

Figure 20B:
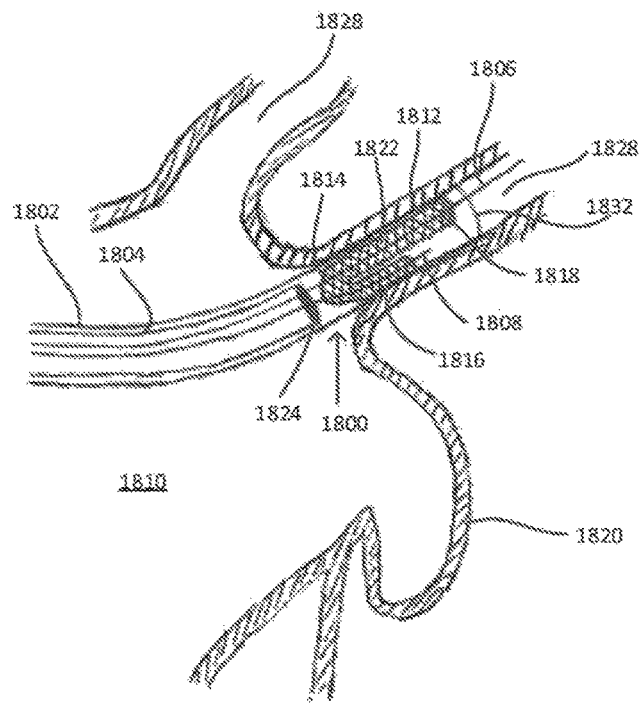
FIG. 20B is a partial cross-sectional view of a left atrium of the human heart of FIG. 20A showing the delivery sheath inserting an inlet portion of the conduit into a pulmonary vein.
Figure 20C:
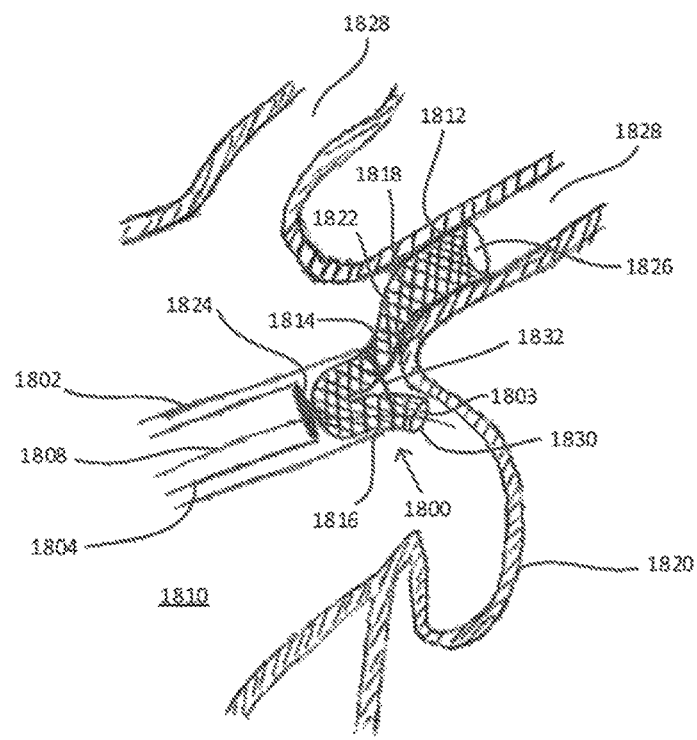
FIG. 20C is a partial cross-sectional view of a left atrium of the human heart of FIG. 20A showing the delivery sheath inserting an outlet portion of the conduit into the LAA.

The delivery sheath 1802 can then be advanced into the pulmonary vein 1828 a distance such that when unsheathed, the frame 1818 of the inlet portion 1812 can expand to anchor the conduit in the pulmonary vein 1828, as shown in FIG. 20B. The inlet portion 1812 can be advanced from the delivery sheath 1802 into the pulmonary vein 1828 using the plunger 1804, and the inlet portion 1812 of the frame 1818 can expand to anchor the inlet portion 1812, as shown in FIG. 20C. With the inlet portion 1812 anchored in the pulmonary vein 1828, the first guide wire 1806 can be withdrawn through the delivery sheath 1802, and the delivery sheath 1802 can be retracted back into the left atrium 1810 and aligned with the ostium of the LAA 1820. During this step, the intermediate and outlet portions 1814, 1816 can remain at least partially contained within the delivery sheath 1802 in a radially compressed or collapsed state, as shown in FIG. 20C. In alternative embodiments, an additional guide wire or member (not shown), such as a guide wire with a hook, or a member with a grasping mechanism, can be used to prevent the folded conduit 1800 from exiting the delivery sheath at this point.

Figure 20D:
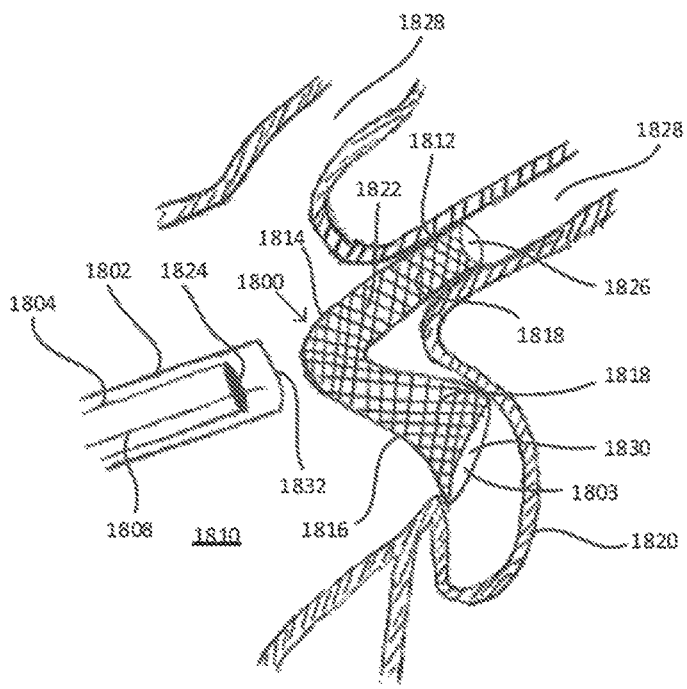
FIG. 20D is a partial cross-sectional view of a left atrium of the human heart of FIG. 20A showing the final placement of the conduit.

Once aligned with the ostium of the LAA 1820, the second guide wire 1808 can be advanced into the LAA 1820 to guide the insertion of the outlet portion 1816. The intermediate and outlet portions 1814, 1816 can then be advanced from the delivery sheath 1802 using the plunger 1804, and the outlet portion 1816 can be guided into the LAA 1820 using the second guide wire 1808. Once in the LAA 1820, the outlet portion 1816 can be expanded such that the outlet portion 1816 is anchored in the LAA 1820. The second guide wire 1808 can then be withdrawn from the LAA 1820 back into the delivery sheath 1802, and the delivery sheath 1802 can be retracted from the left atrium 1810 with the conduit 1800 in a final position, as shown in FIG. 20D.

Figure 21A:
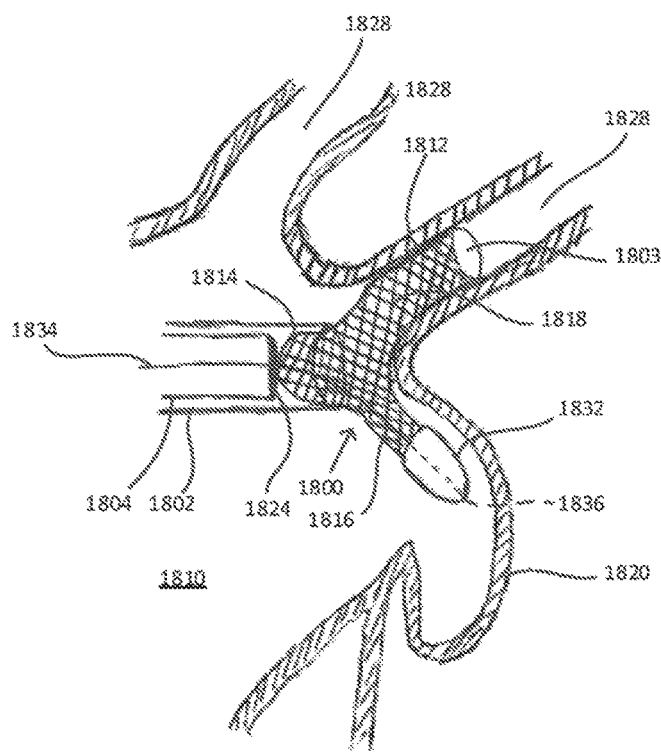
FIG. 21A is a partial cross-sectional view of a left atrium of a human heart showing a delivery sheath containing a conduit having a capped outlet portion, according to another embodiment.
Figure 21B:
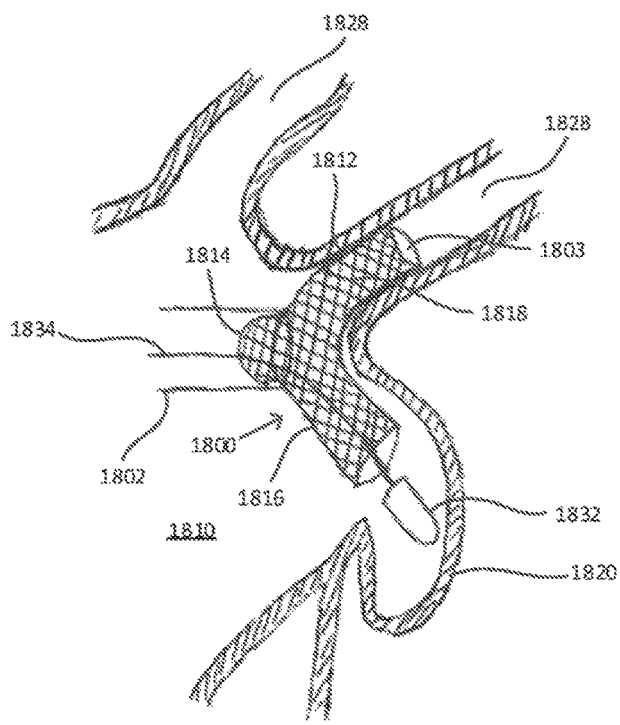
FIG. 21B is a partial cross-sectional view of a left atrium of the human heart of FIG. 21A showing the cap removed from the outlet portion of the conduit.
Figure 22:
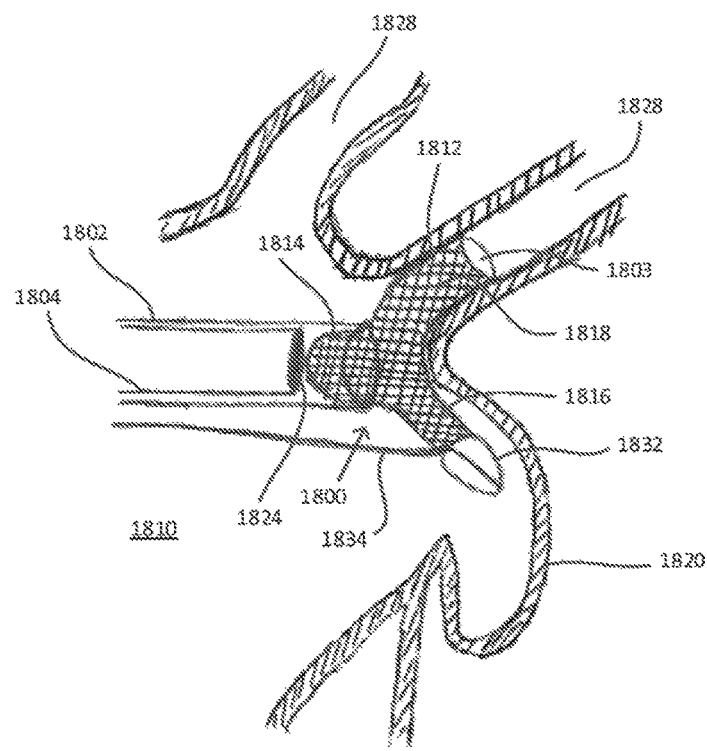
FIG. 22 is a partial cross-sectional view of a left atrium of a human heart showing an alternative embodiment of the conduit of FIG. 21A having a cap with an exterior guide wire.

FIGS. 21A and 21B depict an alternative method of implanting the conduit of FIGS. 20A-20D. FIG. 21A shows the conduit 1800 in mid-implantation with the inlet portion 1812 anchored within the pulmonary vein 1828, as described above. The outlet portion 1816 can be retained in a partially compressed or collapsed state when advanced from the sheath 1802 by a cap or nose cone 1832 that is placed over the outlet portion 1816. The outlet portion 1816 and cap 1832 can be advanced from the delivery sheath 1802 and positioned such that the outlet portion 1816 extends into the LAA 1820. A wire 1834 of the delivery apparatus extends through the plunger 1804, through the intermediate portion 1814, and is attached to an inside surface 1836 (indicated in phantom) of the cap 1832, as shown in FIG. 21A. The wire 1834 can be configured to push the cap 1832 off of the outlet portion 1816, thereby allowing the outlet portion 1816 to expand, as shown in FIG. 21B. The cap 1832 can then be withdrawn through the lumen 1803 of the outlet portion 1816 and through an opening in the intermediate portion 1814 back into the delivery sheath 1802. Alternatively, the wire 1834 can pass outside the delivery sheath 1802, as shown in FIG. 22, eliminating the need to withdraw the cap 1832 through the conduit 1800.

Figure 23:
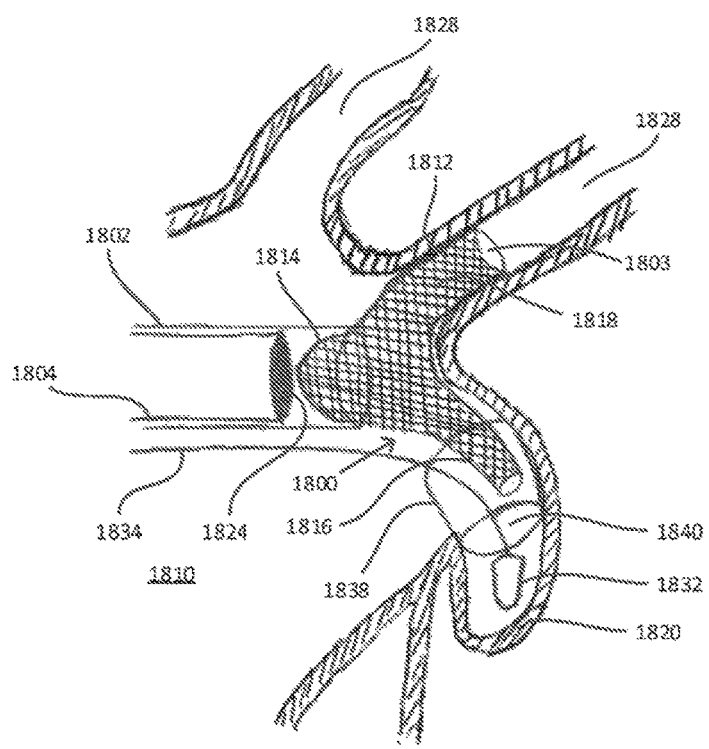
FIG. 23 is a partial cross-sectional view of a left atrium of a human heart showing an alternative embodiment of the conduit of FIG. 21A having a separate anchor and an exterior guide wire.

In another alternative method of implanting the conduit of FIGS. 20A-20D, the cap 1832 can be used in combination with a separate anchor 1838, as shown in FIG. 23. The anchor 1838 can be deployed first inside the LAA 1820 followed by the outlet portion 1816. The anchor 1838 can comprise an expandable stent or frame as discussed above, or a hollow polymeric tube of sufficient diameter to remain immobilized when placed in the LAA 1820. The wire 1834 attached to the cap 1832 can pass outside the delivery sheath 1802 in the manner of the embodiment of FIG. 22, and can be withdrawn through the lumen 1840 of the anchor 1838 after the cap 1832 is removed from the outlet portion 1816. Alternatively, the wire 1834 can pass through the delivery sheath 1802 and through the lumen 1803 of the conduit 1800, as in the embodiment of FIGS. 21A-21B.

Figure 24:
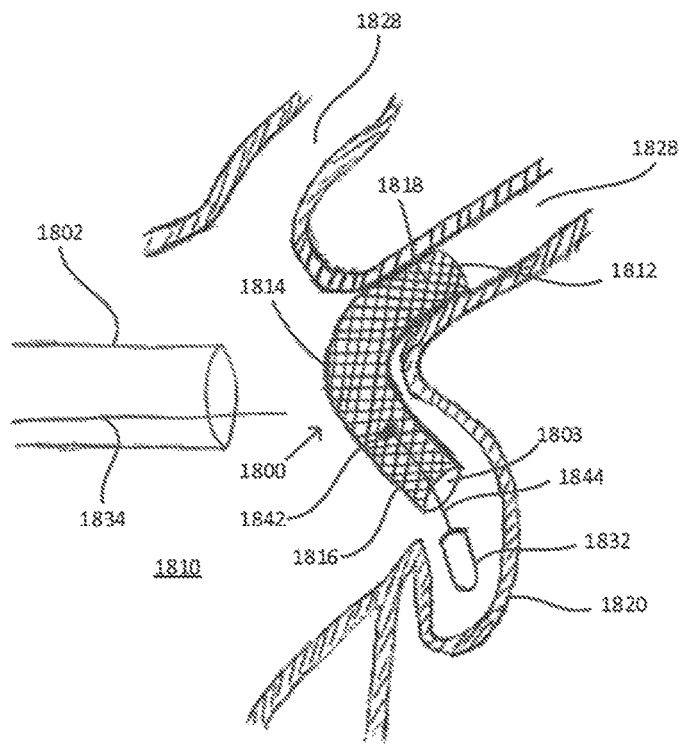
FIG. 24 is a partial cross-sectional view of a left atrium of a human heart showing an alternative embodiment of the conduit of FIG. 21A having a severable guide wire.

In some embodiments, the wire 1834 can be severed by a cutter 1842 at a location inside the outlet portion 1816 after the cap 1832 is pushed off of the outlet portion 1816, as shown in FIG. 24. In this manner, the cap 1832 and a distal end portion 1844 of the wire 1834 can remain inside the LAA 1820. In some embodiments, the distal end portion 1844 of the wire 1834 can remain permanently affixed to the inside of the conduit 1800, eliminating the need to withdraw the cap 1832 through the conduit 1800.

Figure 25A:
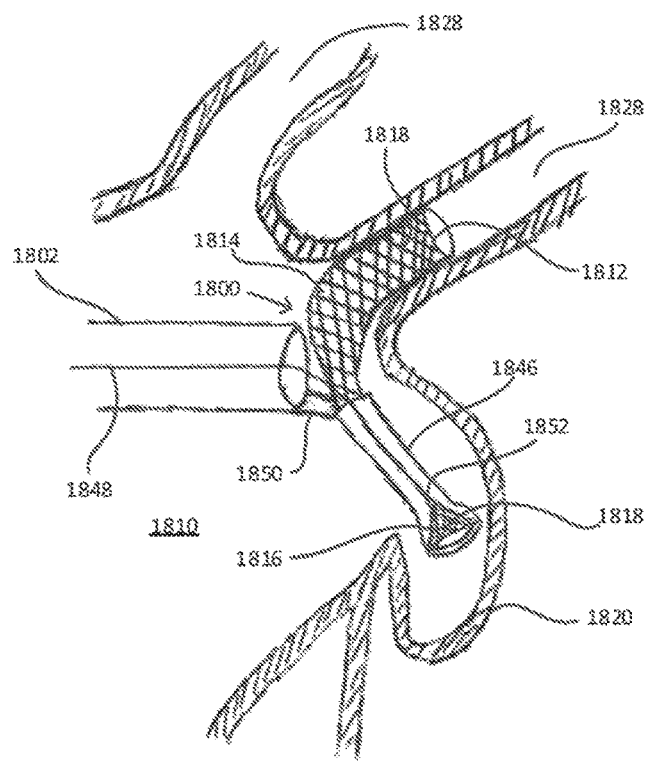
FIG. 25A is a partial cross-sectional view of a left atrium of a human heart showing a conduit having a peel-away sheath and a pull cord.
Figure 25B:
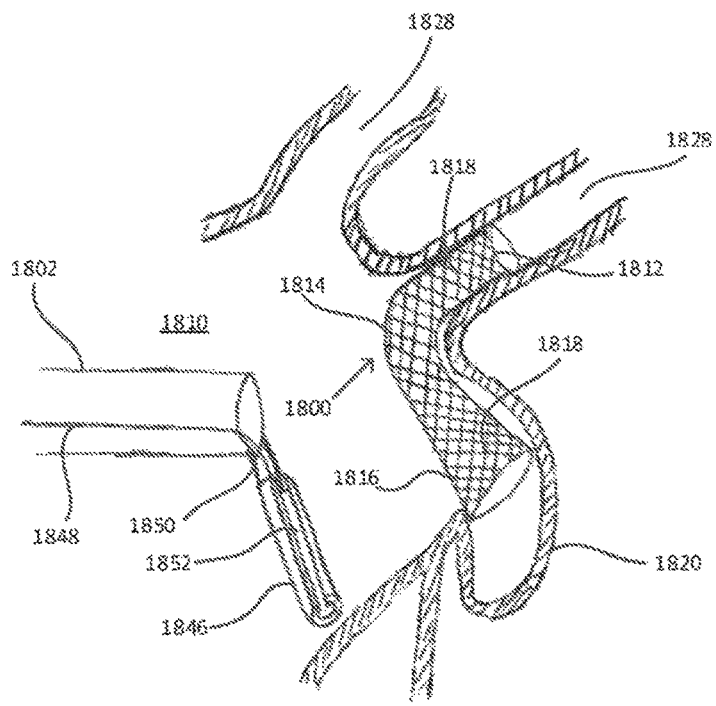
FIG. 25B is a partial cross-sectional view of a left atrium of the human heart of FIG. 25A showing the peel-away sheath removed from the conduit.

FIGS. 25A and 25B illustrate yet another method of implanting the conduit of FIGS. 20A-20D. In addition to providing the delivery sheath 1802 and conduit 1800 as described above, the method comprises providing a peel-away sheath 1846, a pull cord 1848, and a flexible connector 1850. The peel-away sheath 1846 can be disposed around the outlet portion 1816, keeping the outlet portion 1816 in a radially compressed or collapsed state. The flexible connector 1850 serves to attach the peel-away sheath 1846 to the delivery sheath 1802. The pull cord 1848 can be disposed or embedded longitudinally along the peel-away sheath 1846 in such a way that as it is pulled in the direction of the delivery sheath 1802, it opens a slit 1852 in the peel-away sheath 1846, as shown in FIG. 25A. As the slit 1852 opens along the length of the peel-away sheath 1846, the outlet portion 1816 can expand within the LAA 1820. When the pull cord 1848 has propagated the slit 1852 along substantially the entire length of the peel-away sheath 1846, the outlet portion 1816 can be freed from the peel-away sheath 1846 and can expand to anchor the outlet portion 1816 in the LAA 1820, as shown in FIG. 25B. With the peel-away sheath 1846 still attached to the delivery sheath 1802 by the flexible connector 1850, the delivery sheath 1802 and peel-away sheath 1846 assembly can be withdrawn from the left atrium 1810.

Figure 26A:
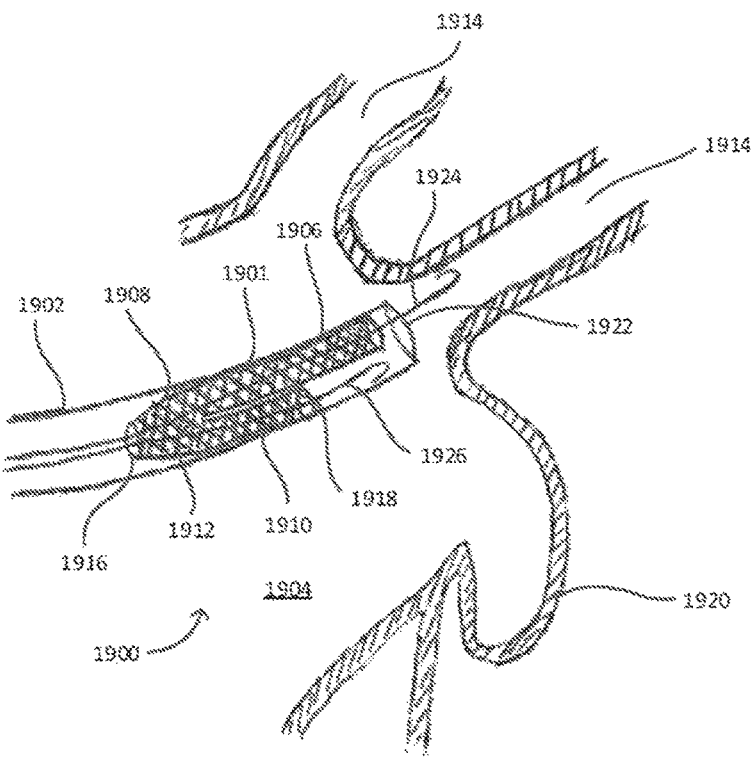
FIG. 26A is a partial cross-sectional view of a left atrium of a human heart showing a delivery sheath containing a conduit having three openings, according to another embodiment.
Figure 26B:
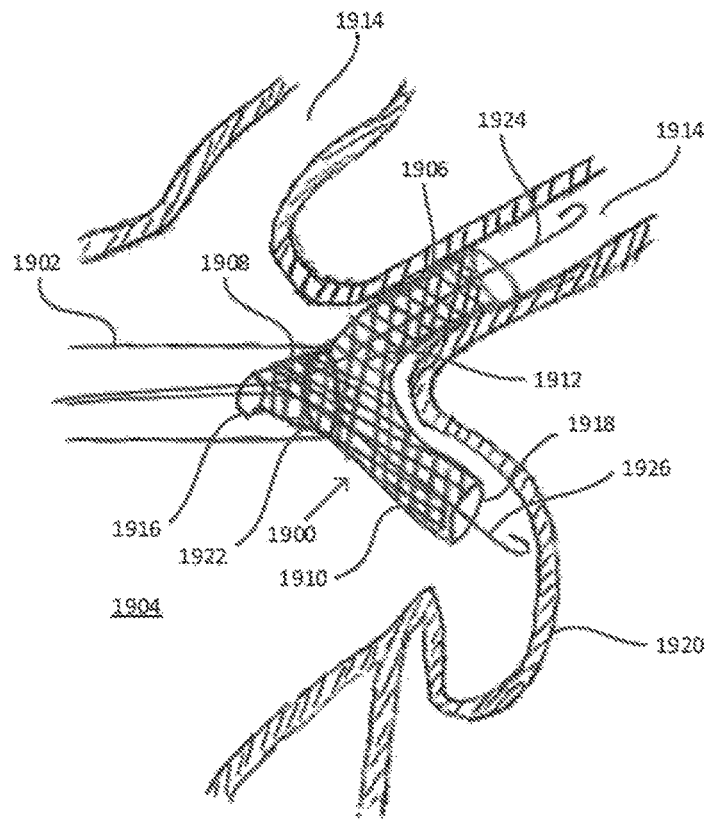
FIG. 26B is a partial cross-sectional view of a left atrium of the human heart of FIG. 26A showing the insertion of an inlet portion and an outlet portion of the conduit in a pulmonary vein and a LAA, respectively.
Figure 26C:
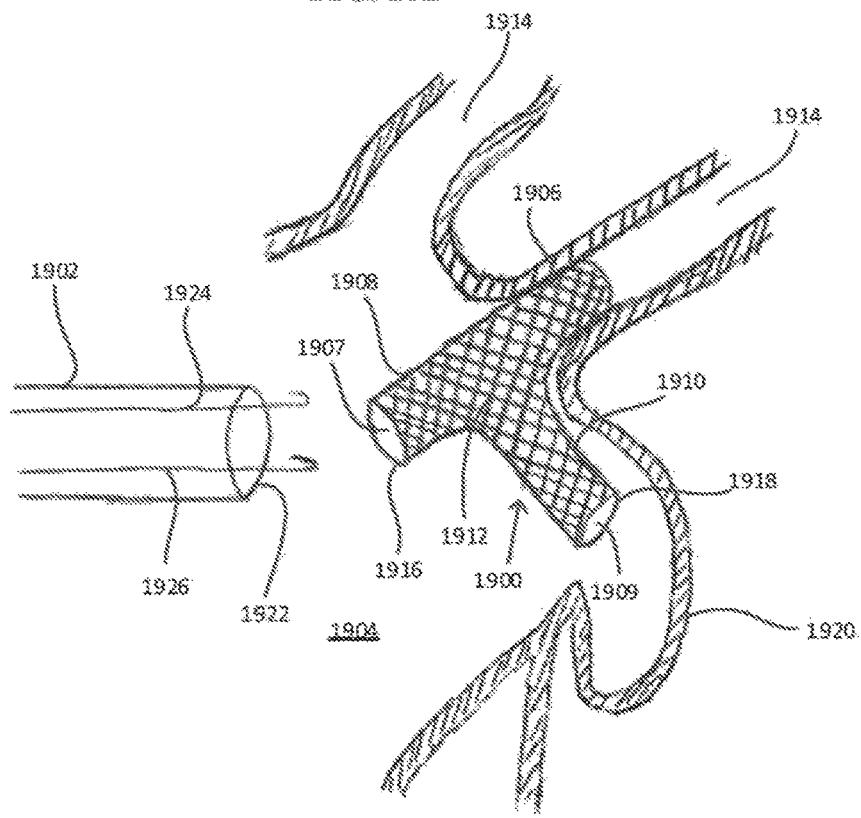
FIG. 26C is a partial cross-sectional view of a left atrium of the human heart of FIG. 26A showing the final placement of the conduit.

FIGS. 26A-26C illustrate a method of implantation of an alternative embodiment of the conduit of FIG. 6. The method comprises providing a conduit 1900 loaded into a delivery sheath 1902, which can access the left atrium 1904 in the manner described above. The conduit 1900 can comprise a generally tubular, T-shaped body 1901 when expanded. As best shown in FIG. 26C, the body 1901 comprises an inlet portion 1906, an outlet portion 1908 and a side branch portion 1910. The inlet, outlet, and side branch portions 1906, 1908, 1910 can be portions of a single frame or stent 1912, which can have the same properties and construction as the frames discussed above. For example, the inlet portion 1906 of the frame 1912 can expand to anchor the conduit in a pulmonary vein 1914. As with the conduit of FIG. 6, the outlet portion 1908 can comprise a generally tubular body defining a lumen 1907 (see FIG. 26C) in fluidic communication with inlet portion 1906 and can be oriented such that a first outlet 1916 points generally in the direction of the left atrium 1904 or the mitral valve (not shown). The side branch portion 1910 can also comprise a generally tubular body defining a lumen 1909 (see FIG. 26C) in communication with the inlet portion 1906, and can be oriented such that a second outlet 1918 points generally in the direction of the LAA 1920.

The conduit 1900 can be loaded into the delivery sheath 1902 in a manner similar to the method of FIGS. 20A-20D, with the conduit 1900 in a radially compressed or collapsed state and folded on itself such that the inlet portion 1906 extends beyond the side branch portion (e.g., the inlet and side branch portions are staggered such that the inlet portion 1906 is closer to the outlet 1922 of the delivery sheath), as shown in FIG. 26A. A first guide wire 1924 originating outside the body can be threaded through the first outlet 1916 of the outlet portion 1908 and outwardly through the inlet portion 1906. From this position, the first guide wire 1924 can be extended into the pulmonary vein 1914 in preparation for unsheathing the conduit. Similarly, a second guide wire 1926, also originating outside the body, can be threaded through the first outlet 1916 and out of the second outlet 1918 of the side branch portion 1910, as shown in FIG. 26A.

The delivery sheath 1902 is first oriented in the left atrium 1904 such that it can be advanced into the pulmonary vein 1914 in preparation for unsheathing the inlet portion 1906 of the conduit, as shown in FIG. 26A. The delivery sheath can then be advanced into the pulmonary vein 1914, the first guide wire 1924 can be advanced through the inlet portion 1906 into the pulmonary vein 1914 to guide insertion, and the inlet portion can be unsheathed. Once unsheathed, the inlet portion 1906 can expand to anchor the inlet portion in the pulmonary vein 1914. Next, the second guide wire 1926 can be advanced through the second outlet 1918 of the side branch portion and into the LAA 1920. After the inlet portion 1906 is unsheathed and anchored in the pulmonary vein 1914, the side branch portion 1910 can be advanced into the LAA 1920 using the second guide wire 1926, as shown in FIG. 26B. Finally, the outlet portion 1908 can be advanced from the delivery sheath 1902 and expanded, after which the first and second guide wires 1924, 1926 can be withdrawn through the outlet portion 1908, and the conduit 1900 can assume its final shape, as shown in FIG. 26C. Alternatively, the conduit 1900 can be advanced from the delivery sheath 1902 with the aid of a plunger in a manner similar to the method of FIGS. 20A-20D.

FIGS. 27A-27D illustrate another method of implanting the conduit of FIGS. 20A-20D. The method comprises providing the conduit 1800 loaded into a delivery sheath 2002, which can access the left atrium 1810 in the manner described above. The delivery sheath 2002 can comprise a generally tubular, flexible body 2004 capable of being folded or bent at any point or points along its length. The delivery sheath 2002 can also include an outlet 2006.

Figure 27A:
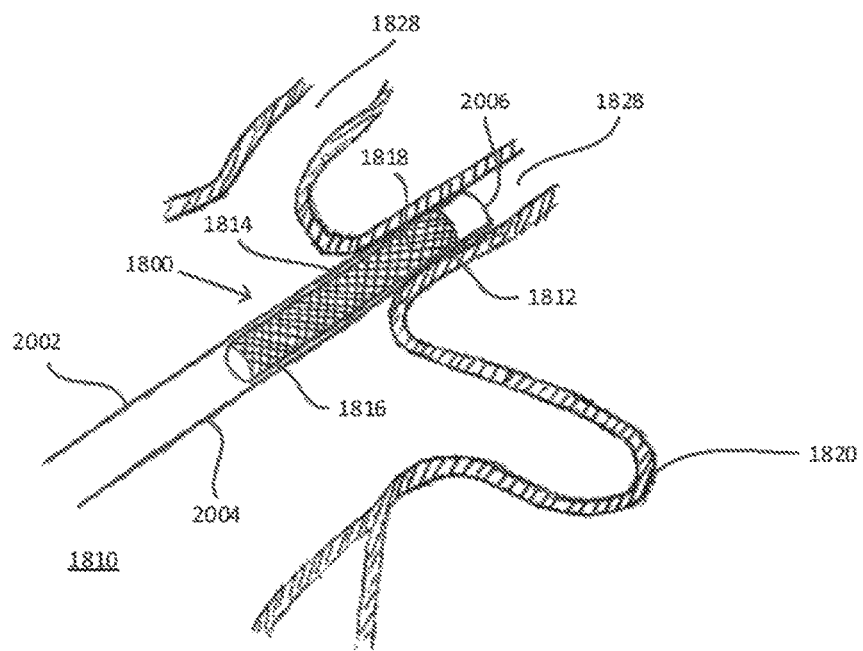
FIG. 27A is a partial cross-sectional view of a left atrium of a human heart showing insertion of an inlet portion of a conduit into a pulmonary vein by a flexible delivery sheath, according to another embodiment.
Figure 27B:
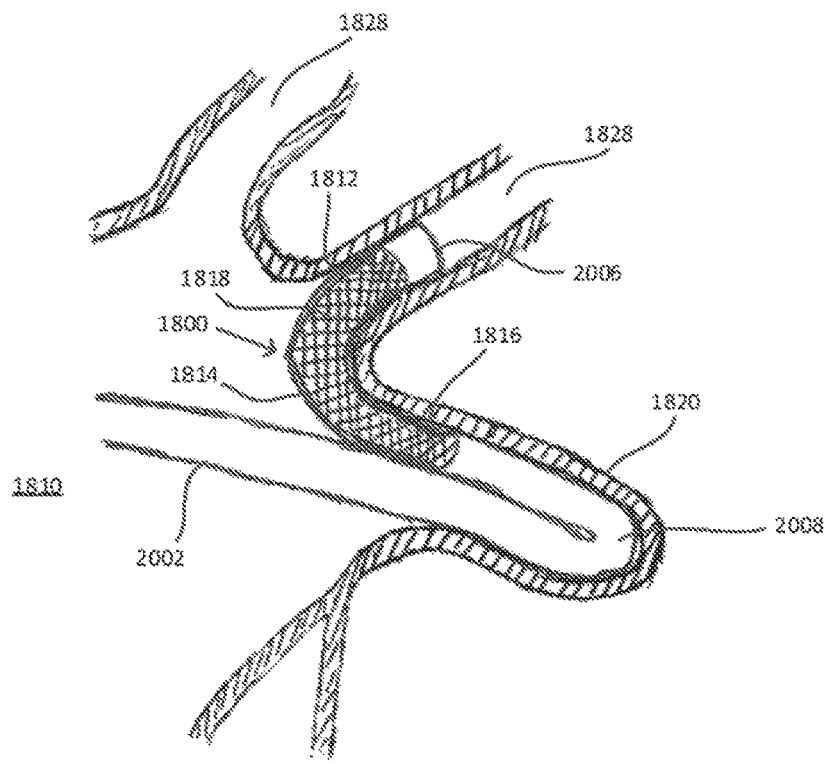
FIG. 27B is a partial cross-sectional view of a left atrium of the human heart of FIG. 27A showing placement of an outlet portion of the conduit into a LAA by folding the flexible delivery sheath into the LAA.
Figure 27C:
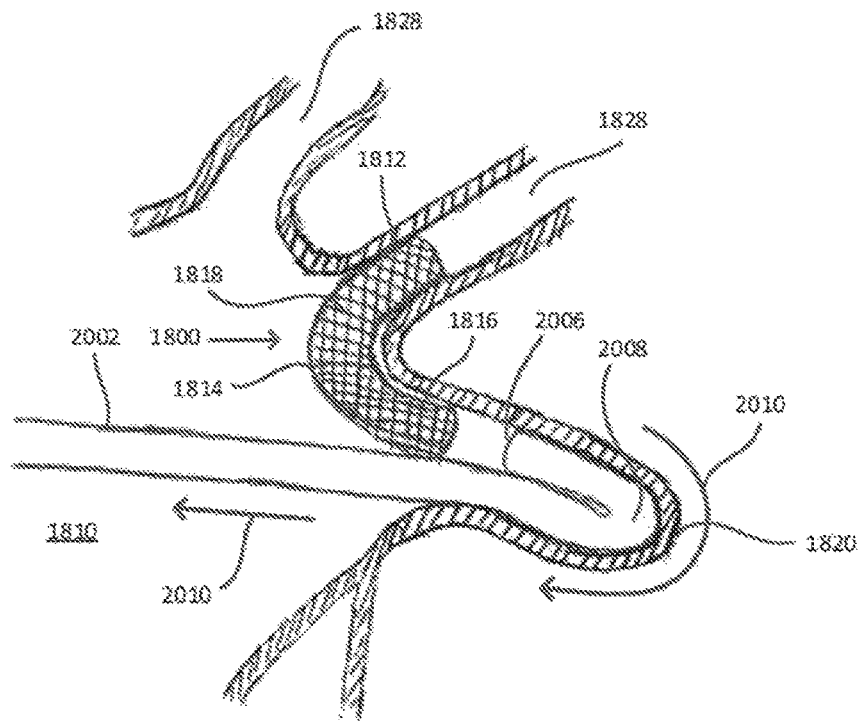
FIG. 27C is a partial cross-sectional view of a left atrium of the human heart of FIG. 27A showing retraction of the flexible delivery sheath through the LAA.
Figure 27D:
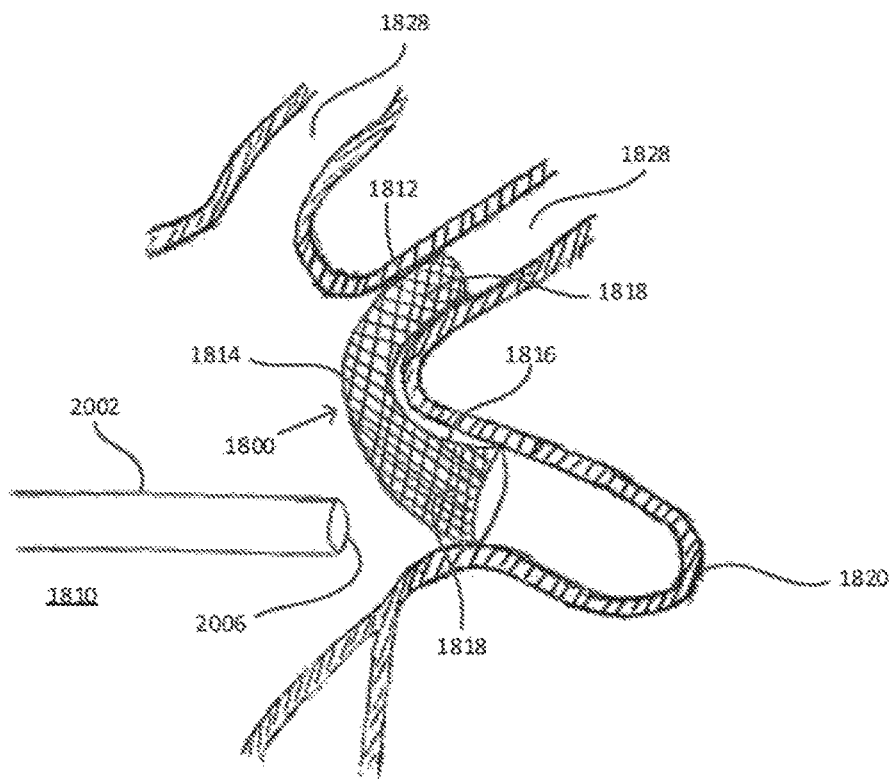
FIG. 27D is a partial cross-sectional view of a left atrium of the human heart of FIG. 27A showing final placement of the conduit.

The conduit 1800 can be loaded into the delivery sheath 2002 in a radially compressed or collapsed state as described above. The delivery sheath 2002 can first be advanced into a pulmonary vein 1828 a distance sufficient to allow the frame 1818 to expand and anchor the inlet portion 1812 in the pulmonary vein 1828 when unsheathed, as shown in FIG. 27A. Without being withdrawn from the pulmonary vein, the delivery sheath 2002 can be urged into the LAA 1820 such that it forms a fold or kink 2008 backward on itself within the LAA 1820, thereby pre-locating the conduit 1800 with the inlet portion 1812 in the pulmonary vein 1828 and the outlet portion 1816 in the LAA 1820, as shown in FIG. 27B. The conduit 1800 can then be unsheathed by withdrawing the delivery sheath 2002 through the LAA 1820 in the direction indicated by arrows 2010 such that the kink 2008 is maintained as the delivery sheath 2002 is withdrawn, as shown in FIG. 27C. As the inlet portion 1812 is exposed from the delivery sheath 2002, the frame 1818 can expand to anchor the inlet portion in the pulmonary vein 1828, as described above. Similarly, after the outlet portion 1816 has been unsheathed and the delivery sheath 2002 has been completely withdrawn from the LAA 1820, the outlet portion 1816 can expand to anchor the conduit in the LAA 1820, as shown in FIG. 27D.

Figure 28:
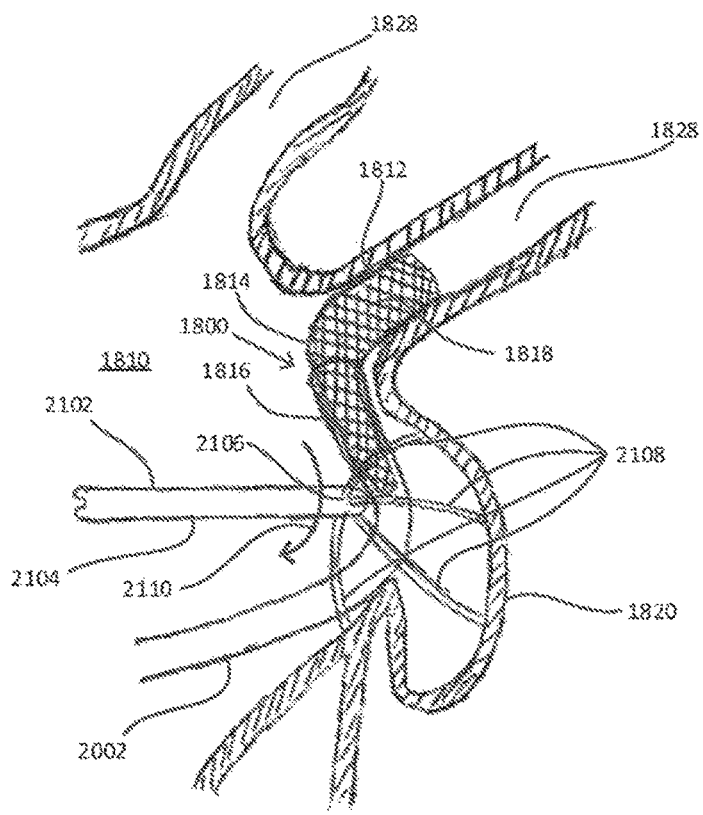
FIG. 28 is a partial cross-sectional view of a left atrium of a human heart showing placement of a conduit in a LAA with a delivery sheath guide tool having a plurality of legs, according to another embodiment.

FIG. 28 illustrates another method of implanting the conduit of FIGS. 20A-20D. The method comprises providing the conduit 1800 loaded in a radially compressed or collapsed state into the delivery sheath 2002 of FIGS. 27A-D, wherein the delivery sheath 2002 can access the left atrium 1810 in the manner discussed above. A guide tool 2102 can be provided having a shaft 2104, a head 2106, and a plurality of legs 2108 disposed about and extending from the head 2106. The guide tool 2102 can access the left atrium 1810 percutaneously in the same manner as the delivery sheath discussed above. The delivery sheath 2002 can first be advanced into the pulmonary vein 1828 a distance sufficient to allow the inlet portion 1812 to expand and anchor the inlet portion 1812 in the pulmonary vein 1828 when unsheathed. The guide tool 2102 can then be used to push the delivery sheath 2002 toward the LAA 1820, causing the delivery sheath 2002 to bend generally in the direction of the LAA 1820, as shown in FIG. 28. The plurality of legs 2108 and the guide tool 2102 can then guide the withdrawal of the delivery sheath 2002 in the direction of the arrow 2110 such that the outlet portion 1816 is drawn into and unsheathed in the LAA 1820.

Figure 29:
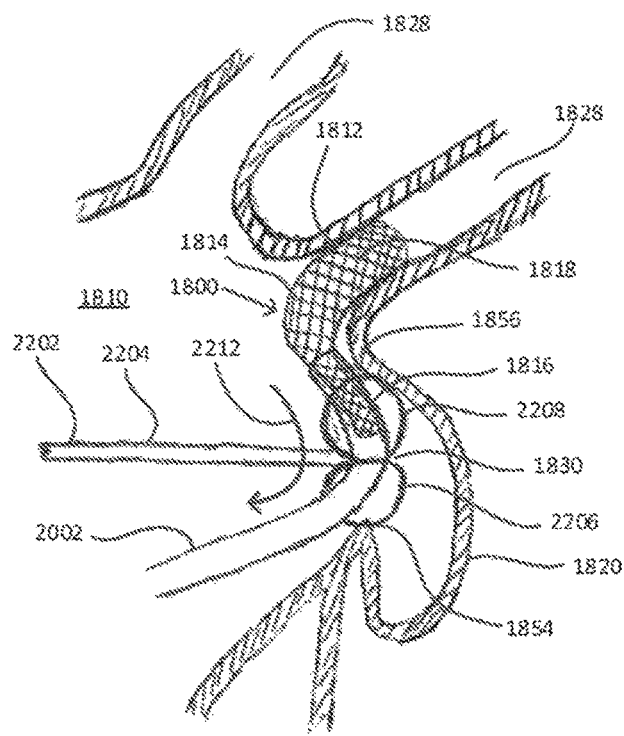
FIG. 29 is a partial cross-sectional view of a left atrium of a human heart showing placement of a conduit in a LAA using another embodiment of a guide tool.

FIG. 29 illustrates yet another method of implanting the conduit of FIGS. 20A-20D. The method comprises providing the conduit 1800 loaded in a radially compressed or collapsed state into the delivery sheath 2002 of FIGS. 27A-27D, wherein the delivery sheath can access the left atrium 1810 in the manner discussed above. A second embodiment of a guide tool 2202 comprises a shaft 2204 that supports a first ring and a second ring 2206, 2208, respectively. The rings 2206, 2208 can be spaced apart from each other in the manner shown in FIG. 29. Although the rings 2206, 2208 are shown having the same diameter, the diameters of the two rings need not be equal.

Prior to deploying the conduit 1800, the guide tool 2202 can be located such that the rings 2206, 2208 are disposed in the ostium 1830 of the LAA 1820 in the manner shown in FIG. 29. In particular, the first ring 2206 can be disposed at the lower boundary 1854 of the ostium 1830, and the second ring 2208 can be disposed at the upper boundary 1856 of the ostium 1830. After the rings 2206, 2208 have been located, the delivery sheath 2002 can be threaded through the rings 2206, 2208 beginning with the first ring 2206 and proceeding through the second ring 2208 into the pulmonary vein 1828. The rings 2206, 2208 can then guide the withdrawal of the delivery sheath 2002 as the conduit 1800 is unsheathed in the direction indicated by arrow 2212. As the conduit 1800 is unsheathed, the inlet portion 1812 expands to anchor the inlet portion 1812 in the pulmonary vein 1828 as discussed above, and the outlet portion 1816 is drawn into and unsheathed and expanded in the LAA 1820, as shown in FIG. 29.

Figure 30A:
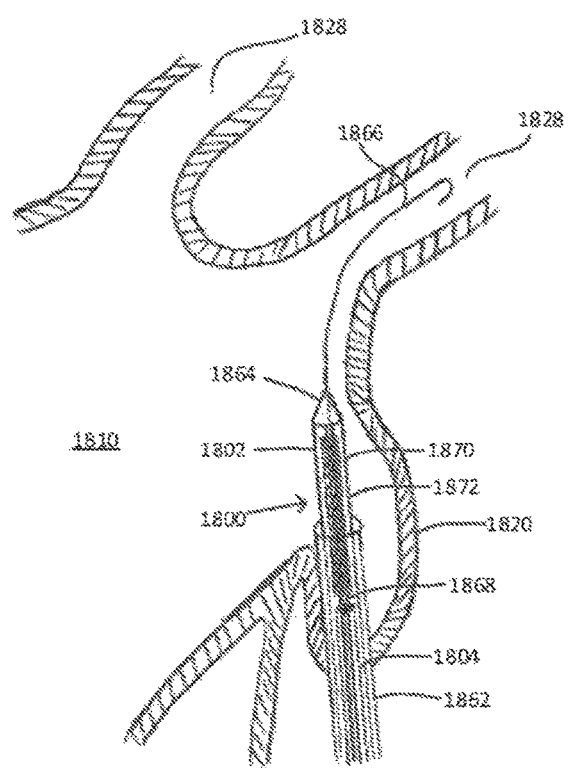
FIG. 30A is a partial cross-sectional view of a left atrium of a human heart showing a delivery sheath entering the left atrium through the LAA wall.
Figure 30B:
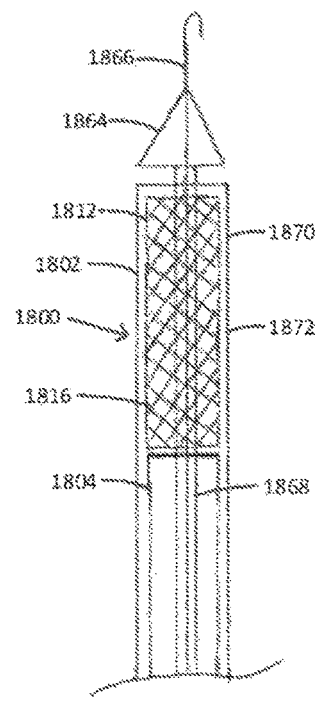
FIG. 30B is a cross-sectional view of a distal end portion of the delivery apparatus of FIG. 30A.
Figure 30C:
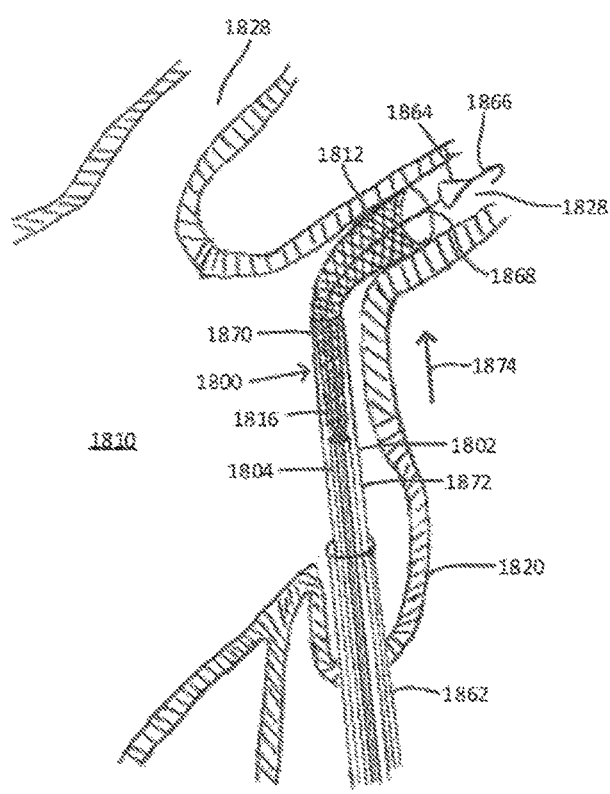
FIG. 30C is a partial cross-sectional view of a left atrium of the human heart of FIG. 30A showing placement of the conduit in a pulmonary vein.

FIGS. 30A-30C illustrate another method of implanting a conduit, such as the conduit 1800 of FIGS. 20A-20D. The conduit 1800 can be contained in a radially collapsed state in a distal end portion 1870 of a delivery apparatus or catheter 1802. The delivery catheter 1802 can comprise an outer shaft 1872 having a distal end portion 1870 that forms a sheath that contains the conduit 1800 in the radially collapsed state. The delivery catheter 1802 can also have a separable cap or tip portion 1864 similar to the caps of FIGS. 21A, 21B, and 22-24, and a pusher member 1804 extending through the outer shaft 1872. As shown in FIG. 30B, a guide wire 1866 can extend through the lumen of a guide wire shaft 1868 contained within the outer shaft 1872 of the delivery catheter 1802. Additionally, the guide wire shaft 1868 can extend through the radially collapsed conduit and the pusher member 1804. In the embodiment shown in FIG. 30B, the guide wire 1866 can also extend through the tip portion 1864, and the tip portion 1864 can be secured to the distal end of the guide wire shaft 1868. Each of the outer shaft 1872, pusher member 1804, and guide wire shaft 1868 can have a respective proximal end coupled to a handle portion (not shown), which can allow the outer shaft 1872, pusher member 1804, and guide wire shaft 1868 to be moved axially (e.g., distally and proximally) relative to each other. The guide wire 1866 can also extend through the guide wire shaft 1868 to the handle portion at the proximal end of the delivery apparatus, and can thereby be manipulated from outside the body.

Referring to FIG. 30A, an introducer 1862 can be inserted through a small incision made in a patient's chest and an incision made in the wall of the LAA 1820. After the introducer 1862 is in place, the delivery catheter 1802 can be inserted through the introducer 1862 and advanced into the LAA 1820 generally in the direction of a pulmonary vein 1828. As shown in FIG. 30C, the distal end of the catheter 1802 can be advanced into the pulmonary vein 1828, where the tip portion 1864 can be removed by advancing the guide wire shaft 1868 in the distal direction, as indicated by arrow 1874. The pusher member 1804 can then be employed to push the conduit 1800 out of the distal end of the outer shaft 1872, allowing the inlet portion 1812 of the conduit 1800 to expand and anchor the conduit 1800 in the pulmonary vein 1828. Once the inlet portion 1812 is anchored in position, the pusher member 1804 can then push the remainder of the conduit 1800 out of the distal end of the outer shaft 1872. In some embodiments, the outlet portion 1816 of the conduit 1800 is deployed and expanded within the LAA 1820. Once the conduit 1800 has expanded to its final size and orientation, the tip portion 1864 and the guide wire shaft 1868 can be withdrawn through the conduit 1800.

In alternative embodiments, the conduit 1800 can be deployed from the outer shaft 1872 by holding the pusher member 1804 stationary and retracting the outer shaft 1872 in the proximal direction, rather than pushing the pusher member 1804 distally relative to the outer shaft 1872. In further alternative embodiments, the conduit 1800 can be plastically expandable, and can be crimped onto a balloon (or other type of expansion device) at the distal end portion of the delivery catheter 1802. Once the conduit 1800 is positioned at a desired deployment location (e.g., the inlet portion 1812 of the conduit 1800 is in the pulmonary vein 1828 and the outlet portion 1816 of the conduit 1800 is in the LAA 1820), the balloon can be inflated to expand the conduit 1800 to its functional size. Additionally, it should be understood that implanting a conduit by advancing a delivery catheter through the LAA wall is generally applicable to any of the embodiments described herein.

Figure 34:
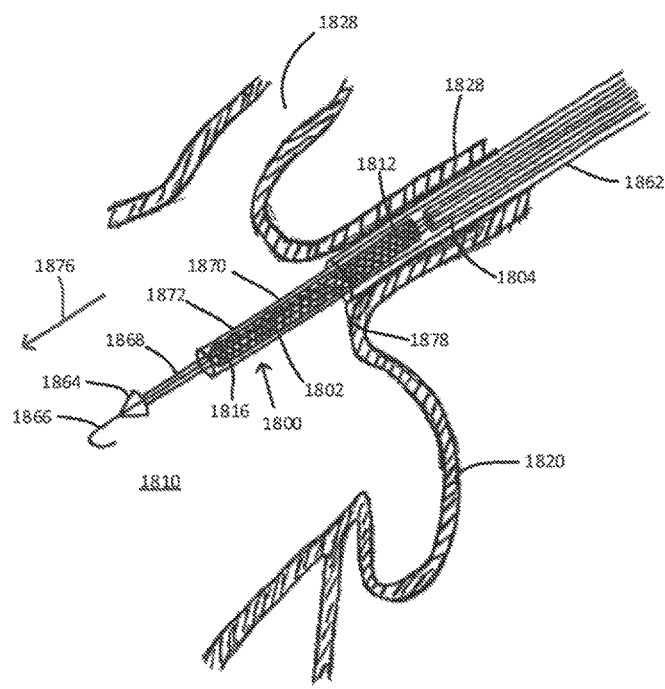
FIG. 34 is a partial cross-sectional view of a left atrium of a human heart illustrating a method of implanting a conduit through a pulmonary vein.

FIG. 34 illustrates another method of implanting the conduit 1800 using the delivery catheter 1802 of FIGS. 20A-20D in which the conduit 1800 is implanted via a pulmonary vein 1828. The conduit 1800 can be in a radially collapsed state in the distal end portion 1870 of the delivery catheter 1802, with the outlet portion 1816 of the conduit 1800 located toward the distal end of the delivery catheter 1802. The introducer 1862 can be advanced percutaneously through the patient's vasculature until a distal end portion 1878 of the introducer 1862 is located in the pulmonary vein 1828, as shown in FIG. 34. The delivery catheter 1802 can then be inserted through the introducer 1862 and advanced into the left atrium 1810 until the inlet portion 1812 of the conduit 1800 is located a sufficient distance within the pulmonary vein 1828 such that when expanded, the conduit 1800 can be anchored in the pulmonary vein 1828. The pusher member 1804 can be positioned such that the pusher member 1804 is in contact with the inlet portion 1812 of the conduit 1800. The guide wire shaft 1868 can then be advanced in a distal direction indicated by arrow 1876, thereby removing the tip portion 1864 from the delivery catheter 1802.

The delivery catheter 1802 can then be withdrawn, followed by the introducer 1862, while the pusher member 1804 remains in contact with the inlet portion 1812 of the conduit 1800. When the distal end portion 1878 of the introducer 1862 reaches the pusher member 1804, the pusher member 1804 and the introducer 1862 can be withdrawn together. In this manner, the conduit 1800 can be unsheathed and allowed to expand to its functional size and orientation. With the inlet portion 1812 of the conduit 1800 anchored in the pulmonary vein 1828, the tip portion 1864 and the guide wire shaft 1868 can then be withdrawn through the conduit 1800, as described above.

Figure 35:
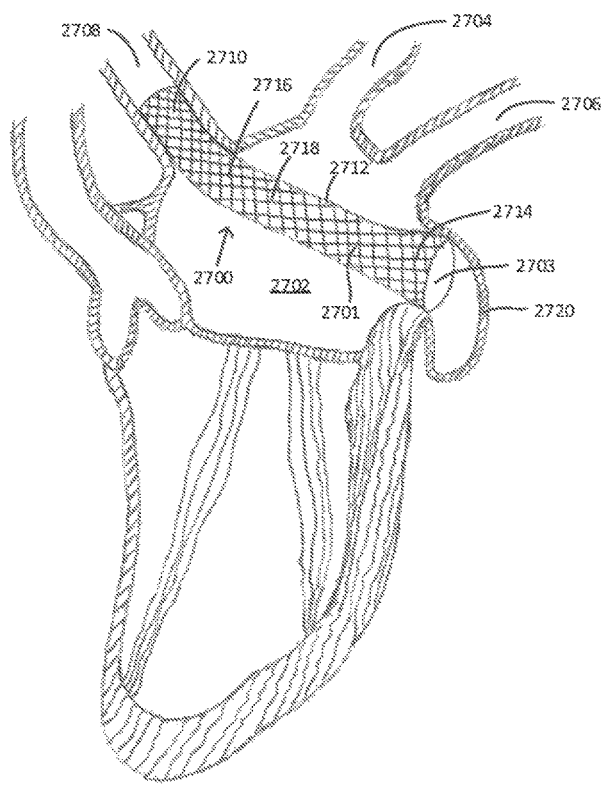
FIG. 35 is a partial cross-sectional view of a left atrium showing an embodiment of a conduit with an inlet anchored in a right pulmonary vein and an outlet in the left atrial appendage.

FIG. 35 illustrates another embodiment of a conduit 2700 located in a cross-section of a left atrium 2702 of a human heart. The left atrium 2702 includes a left superior pulmonary vein 2704, a left inferior pulmonary vein 2706, a right superior pulmonary vein 2708, and a right inferior pulmonary vein (not shown). Although the left atrium 2702 includes right superior and right inferior pulmonary veins, only the right superior pulmonary vein 2708 is shown for convenience of illustration. Thus, it should be understood that the following discussion is applicable to both the right superior and right inferior pulmonary veins.

The conduit 2700 comprises a generally tubular body or sleeve 2701 defining a lumen 2703, and includes an inlet portion 2710, an intermediate portion 2712, and an outlet portion 2714. The inlet, intermediate, and outlet portions 2710, 2712, 2714 can be portions of a single frame or stent 2716, which can have the same properties and construction as the frames discussed above. The inlet portion 2710 can be located in the right superior pulmonary vein 2708, and can expand to anchor the conduit 2700 in the right superior pulmonary vein 2708. Similarly, the outlet portion 2714 can be located in or adjacent the LAA 2720, and can expand to anchor the conduit 2700 in the LAA 2720. In this manner, the conduit 2700 can extend across the left atrium 2702.

The relatively small angle between the right superior pulmonary vein 2708 and the LAA 2720 can allow the conduit 2700 to direct a flow of blood from the right superior pulmonary vein 2708 to the LAA 2720 while minimizing the degree of curvature of the conduit 2700, which can improve the flow characteristics within the conduit. Implantation in the right superior pulmonary vein 2708 can also allow blood flow from the left superior and left inferior pulmonary veins 2704, 2706 and/or the right inferior pulmonary vein (not shown) to bathe the conduit 2700. This can reduce the risk of thrombi formation on the exterior of the conduit 2700. The conduit 2700 can be implanted in the right superior pulmonary vein 2708 or the right inferior pulmonary vein in accordance with any of the delivery methods described above. Additionally, any of the conduits described herein can be configured to be implanted in the right superior and right inferior pulmonary veins in the manner described above.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of implanting a prosthetic conduit in a heart, comprising:
   inserting a distal end portion of a delivery catheter into a left atrium of the heart, the prosthetic conduit being carried in a radially compressed or collapsed state by the distal end portion of the delivery catheter;
   expanding an inlet portion of the prosthetic conduit in a left atrial appendage such that the inlet portion of the prosthetic conduit becomes anchored within the left atrial appendage and directs blood in the left atrial appendage to flow through a lumen of the prosthetic conduit and outwardly through an outlet portion of the prosthetic conduit; and
   locating the outlet portion in the left atrium such that the outlet portion extends outwardly from an ostium of the left atrial appendage toward a mitral valve such that a flow of blood from the outlet portion is directed to flow in a direction toward the mitral valve.

2. The method of claim 1, wherein the flow of blood through the prosthetic conduit is induced by a difference in pressure between the inlet portion and the outlet portion of the prosthetic conduit as blood flows from the left atrium through the mitral valve to a left ventricle.

3. The method of claim 1, wherein the inlet portion comprises an expandable frame, and expanding the inlet portion further comprises expanding the frame in the left atrial appendage.

4. The method of claim 3, wherein:
   the frame comprises an inflow portion configured to anchor the prosthetic conduit in the left atrial appendage; and
   the frame further comprises a tapered outlet portion coupled to a main body of the conduit and having a diameter that is less than a diameter of the inlet portion of the frame.

5. The method of claim 3, wherein the outlet portion of the frame comprises openings configured to allow blood to flow into the left atrial appendage through the frame.

6. The method of claim 3, wherein expanding the frame further comprises expanding the frame such that the frame contacts walls of the left atrial appendage while leaving at least a portion of an ostium of the left atrial appendage open such that blood can flow into or out of the left atrial appendage around the conduit.

7. The method of claim 1, wherein the expanding and the locating further comprise releasing the prosthetic conduit from a sheath of the delivery catheter so that the prosthetic conduit assumes a predetermined curved shape.

8. The method of claim 1, wherein:
   the conduit comprises a plurality of annular hoops; and
   a covering extending over at least a portion of the plurality of annular hoops.

9. The method of claim 1, wherein the inlet portion comprises a flared shape.

10. A method of implanting a conduit in a heart, comprising:
    anchoring an inlet portion of the conduit within a left atrial appendage such that the conduit extends outwardly from an ostium of the left atrial appendage into a left atrium in a direction toward a mitral valve and directs a flow of blood from the left atrial appendage through a lumen of the conduit and outwardly through an outlet portion of the conduit in a direction toward the mitral valve.

11. The method of claim 10, wherein the inlet portion comprises an expandable frame, and anchoring the inlet portion further comprises expanding the frame in the left atrial appendage.

12. The method of claim 11, wherein:
    the frame comprises an inflow portion configured to anchor the prosthetic conduit in the left atrial appendage; and
    the frame further comprises a tapered outlet portion coupled to a main body of the conduit and having a diameter that is less than a diameter of the inlet portion of the frame.

13. The method of claim 11, wherein the outlet portion of the frame comprises openings configured to allow blood to flow into the left atrial appendage through the frame.

14. The method of claim 10, wherein anchoring the inlet portion further comprises anchoring the inlet portion such that the inlet portion contacts walls of the left atrial appendage while leaving at least a portion of an ostium of the left atrial appendage open such that blood can flow into or out of the left atrial appendage around the conduit.

15. The method of claim 10, further comprising releasing the prosthetic conduit from a sheath of a delivery catheter so that the prosthetic conduit assumes a predetermined curved shape.

16. The method of claim 10, wherein:
   the conduit comprises a plurality of annular hoops; and
   a covering extending over at least a portion of the plurality of annular hoops.

17. The method of claim 10, wherein the inlet portion comprises a flared shape.

18. The method of claim 10, further comprising locating an outlet portion of the conduit in a left ventricle.

19. A method of implanting a conduit in a heart, comprising:
   anchoring an inlet portion of the conduit within a left atrial appendage such that the conduit extends outwardly from the left atrial appendage into a left atrium and directs a flow of blood from the left atrial appendage through a lumen of the conduit and outwardly through an outlet portion of the conduit in a direction toward the left atrium, and such that the inlet portion contacts walls of the left atrial appendage while leaving at least a portion of an ostium of the left atrial appendage open such that blood can flow into or out of the left atrial appendage around the conduit.

20. The method of claim 19, further comprising releasing the prosthetic conduit from a sheath of a delivery catheter so that the prosthetic conduit assumes a predetermined curved shape.

* * * * *